US010390867B2

(12) United States Patent
Sixto et al.

(10) Patent No.: US 10,390,867 B2
(45) Date of Patent: Aug. 27, 2019

(54) BONE PLATE SYSTEM AND METHOD

(71) Applicant: Biomet C.V., Gibraltar (GI)

(72) Inventors: Robert Sixto, Miami, FL (US); Juergen Kortenbach, Miami Springs, FL (US); Jose Luis Francese, Miami Springs, FL (US)

(73) Assignee: Biomet C.V., Warsaw, IN (US)

( * ) Notice: Subject to any disclaimer, the term of this patent is extended or adjusted under 35 U.S.C. 154(b) by 198 days.

(21) Appl. No.: 14/471,565

(22) Filed: Aug. 28, 2014

(65) Prior Publication Data
US 2014/0371799 A1 Dec. 18, 2014

Related U.S. Application Data

(60) Continuation-in-part of application No. 14/230,548, filed on Mar. 31, 2014, now Pat. No. 9,757,171, (Continued)

(51) Int. Cl.
*A61B 17/80* (2006.01)
*A61B 17/86* (2006.01)
(Continued)

(52) U.S. Cl.
CPC ...... *A61B 17/8057* (2013.01); *A61B 17/8014* (2013.01); *A61B 17/8061* (2013.01);
(Continued)

(58) Field of Classification Search
CPC . A61B 17/7059; A61B 17/80; A61B 17/8004; A61B 17/8014; A61B 17/8052;
(Continued)

(56) References Cited

U.S. PATENT DOCUMENTS 3,716,050 A    2/1973   Johnston
3,770,119 A    11/1973   Hultberg et al.
(Continued)

FOREIGN PATENT DOCUMENTS

AU     2010295518 B2    9/2016
CN     1337864 A        2/2002
(Continued)

OTHER PUBLICATIONS

Catalog 0612-24-508 "ALP.S. Anatomic Locking Plate System", © 2009, DePuy Orthopaedics, Inc., 700 Orthopaedic Dr., Warsaw, IN 46581-0988, USA.
(Continued)

*Primary Examiner* — Christopher J Beccia
(74) *Attorney, Agent, or Firm* — Schwegman Lundberg & Woessner, P.A.

(57) ABSTRACT

A bone plate system and method for implanting the bone plate. The bone plate may include a head portion and a shaft portion, the shaft portion having a longitudinal axis and comprising a plurality of discrete aperture clusters. Each aperture cluster may include a non-threaded, non-locking bone fastener aperture configured to provide a polyaxial compressive construct and at least one threaded, locking bone fastener aperture. Once aligned with the bone, a first bone fastener is inserted into the bone through at least one of the non-threaded apertures in a direction normal to the longitudinal axis, compressing the bone along the longitudinal axis of the shaft portion of the bone plate. A second bone fastener is inserted into the bone through at least one of the threaded, locking bone fastener apertures in a direction oblique to the longitudinal axis and securing the bone plate to the bone.

17 Claims, 33 Drawing Sheets

Related U.S. Application Data which is a division of application No. 12/884,242, filed on Sep. 17, 2010, now Pat. No. 8,685,068.

(60) Provisional application No. 61/243,752, filed on Sep. 18, 2009.

(51) Int. Cl.

| | | |
|---|---|---|
| *A61B 17/88* | (2006.01) | |
| *A61B 50/30* | (2016.01) | |
| *A61B 50/36* | (2016.01) | |
| *A61B 17/17* | (2006.01) | |
| *A61B 17/90* | (2006.01) | |
| *A61B 50/00* | (2016.01) | |
| *A61B 50/20* | (2016.01) | |
| *A61B 50/33* | (2016.01) | |
| *A61B 90/00* | (2016.01) | |

(52) U.S. Cl.
CPC ............ *A61B 17/86* (2013.01); *A61B 17/865* (2013.01); *A61B 17/8615* (2013.01); *A61B 17/888* (2013.01); *A61B 50/30* (2016.02); *A61B 50/36* (2016.02); *A61B 17/1728* (2013.01); *A61B 17/1739* (2013.01); *A61B 17/1782* (2016.11); *A61B 17/8052* (2013.01); *A61B 17/8605* (2013.01); *A61B 50/20* (2016.02); *A61B 50/33* (2016.02); *A61B 2017/90* (2013.01); *A61B 2050/008* (2016.02); *A61B 2050/0051* (2016.02); *A61B 2050/0056* (2016.02); *A61B 2050/0065* (2016.02); *A61B 2050/0066* (2016.02); *A61B 2050/3008* (2016.02); *A61B 2090/062* (2016.02)

(58) Field of Classification Search
CPC . A61B 17/8057; A61B 17/8061; A61B 17/84; A61B 17/86; A61B 17/8605; A61B 17/862
USPC .......................................... 606/280–299, 915
See application file for complete search history.

(56) References Cited

U.S. PATENT DOCUMENTS

| | | | |
|---|---|---|---|
| 4,332,502 A | 6/1982 | Wormald et al. | |
| 4,513,744 A | 4/1985 | Klaue | |
| 4,596,329 A | 6/1986 | Eldridge, Jr. | |
| 5,040,676 A | 8/1991 | Bell | |
| 5,275,601 A | 1/1994 | Gogolewski et al. | |
| 5,569,247 A | 10/1996 | Morrison | |
| 5,601,553 A | 2/1997 | Trebing et al. | |
| 5,690,222 A | 11/1997 | Peters | |
| 5,690,489 A | 11/1997 | Carchidi | |
| 5,709,686 A | 1/1998 | Talos et al. | |
| 5,732,821 A | 3/1998 | Stone et al. | |
| 5,791,472 A | 8/1998 | Davis | |
| 5,807,396 A | 9/1998 | Raveh et al. | |
| 5,848,693 A | 12/1998 | Davis et al. | |
| 5,881,878 A | 3/1999 | Faccioli et al. | |
| 6,017,177 A | 1/2000 | Lanham | |
| 6,096,040 A | 8/2000 | Esser | |
| 6,161,695 A | 12/2000 | Nicolais | |
| 6,164,044 A | 12/2000 | Porfano et al. | |
| 6,189,292 B1 | 2/2001 | Odell et al. | |
| 6,250,052 B1 | 6/2001 | Porfano et al. | |
| 6,263,641 B1 | 7/2001 | Odell et al. | |
| 6,322,562 B1 | 11/2001 | Wolter | |
| 6,365,115 B1 | 4/2002 | Wood | |
| 6,426,041 B1 | 7/2002 | Smith | |
| 6,623,486 B1* | 9/2003 | Weaver et al. | ............... 606/281 |
| 6,695,882 B2 | 2/2004 | Bianchi et al. | |
| 6,730,091 B1 | 5/2004 | Pfefferle et al. | |
| 6,813,978 B1 | 11/2004 | Karpp | |
| 6,960,211 B1 | 11/2005 | Pfefferle et al. | |
| 6,974,461 B1 | 12/2005 | Wolter | |
| 7,128,744 B2 | 10/2006 | Weaver et al. | |
| 7,137,987 B2 | 11/2006 | Patterson et al. | |
| 7,175,624 B2 | 2/2007 | Konieczynski et al. | |
| 7,179,260 B2 | 2/2007 | Gerlach et al. | |
| 7,350,643 B2 | 4/2008 | Capanni et al. | |
| 7,354,441 B2 | 4/2008 | Frigg | |
| 7,549,270 B2 | 6/2009 | Rowe et al. | |
| 8,496,690 B2 | 7/2013 | Sixto et al. | |
| 8,685,068 B2 | 4/2014 | Sixto et al. | |
| 8,790,378 B2 | 7/2014 | Castaneda et al. | |
| 9,757,171 B2 | 9/2017 | Sixto et al. | |
| 2002/0004660 A1 | 1/2002 | Henniges et al. | |
| 2002/0045901 A1 | 4/2002 | Wagner et al. | |
| 2002/0052605 A1 | 5/2002 | Grooms et al. | |
| 2004/0019353 A1 | 1/2004 | Freid et al. | |
| 2004/0030339 A1 | 2/2004 | Wack et al. | |
| 2004/0167522 A1 | 8/2004 | Niederberger et al. | |
| 2004/0200754 A1 | 10/2004 | Hagemeier | |
| 2004/0236332 A1 | 11/2004 | Frigg | |
| 2004/0260291 A1 | 12/2004 | Jensen | |
| 2005/0015089 A1 | 1/2005 | Young et al. | |
| 2005/0033430 A1 | 2/2005 | Powers et al. | |
| 2005/0059971 A1 | 3/2005 | Michelson | |
| 2005/0070904 A1 | 3/2005 | Gerlach et al. | |
| 2005/0137597 A1 | 6/2005 | Butler et al. | |
| 2005/0165400 A1 | 7/2005 | Fernandez | |
| 2005/0173278 A1 | 8/2005 | Caron | |
| 2005/0234472 A1 | 10/2005 | Huebner | |
| 2005/0261688 A1 | 11/2005 | Grady, Jr. | |
| 2006/0004362 A1 | 1/2006 | Patterson et al. | |
| 2006/0009771 A1 | 1/2006 | Orbay et al. | |
| 2006/0122603 A1 | 6/2006 | Kolb | |
| 2006/0149250 A1 | 7/2006 | Castaneda et al. | |
| 2006/0173459 A1 | 8/2006 | Kay et al. | |
| 2006/0231443 A1 | 10/2006 | Jonasson et al. | |
| 2006/0243616 A1 | 11/2006 | Caron | |
| 2006/0264946 A1 | 11/2006 | Young | |
| 2006/0266168 A1 | 11/2006 | Pacheco | |
| 2007/0016205 A1 | 1/2007 | Beutter et al. | |
| 2007/0233114 A1 | 10/2007 | Bouman | |
| 2007/0239163 A1* | 10/2007 | Strnad et al. | ................... 606/72 |
| 2007/0260244 A1 | 11/2007 | Wolter | |
| 2008/0051786 A1 | 2/2008 | Jensen | |
| 2008/0091198 A1 | 4/2008 | Leibel et al. | |
| 2008/0116106 A1 | 5/2008 | Lampropoulos et al. | |
| 2008/0140130 A1 | 6/2008 | Chan et al. | |
| 2008/0154281 A1 | 6/2008 | Schaffran et al. | |
| 2009/0018588 A1 | 1/2009 | Eckhof et al. | |
| 2009/0018589 A1 | 1/2009 | Smisson, III et al. | |
| 2009/0118768 A1* | 5/2009 | Sixto, Jr. | ............ A61B 17/8061 606/280 |
| 2009/0171399 A1 | 7/2009 | White et al. | |
| 2009/0223851 A1 | 9/2009 | Jacobs et al. | |
| 2009/0254126 A1 | 10/2009 | Orbay et al. | |
| 2009/0326545 A1 | 12/2009 | Schaffhausen | |
| 2010/0140124 A1 | 6/2010 | Hafner | |
| 2010/0154353 A1 | 6/2010 | Cesa et al. | |
| 2010/0300910 A1 | 12/2010 | Hawkes | |
| 2011/0071572 A1 | 3/2011 | Sixto et al. | |
| 2011/0071573 A1 | 3/2011 | Sixto et al. | |
| 2014/0214091 A1 | 7/2014 | Sixto et al. | |

FOREIGN PATENT DOCUMENTS

| | | |
|---|---|---|
| CN | 1373646 A | 10/2002 |
| CN | 101175449 A | 5/2008 |
| CN | 101883532 A | 11/2010 |
| CN | 102630155 A | 8/2012 |
| CN | 107072678 A | 8/2017 |
| DE | 20318732 U1 | 2/2004 |
| EP | 58219 A1 | 8/1982 |
| EP | 207884 A2 | 1/1987 |
| EP | 1191890 A1 | 4/2002 |
| EP | 1474055 A1 | 11/2004 |
| EP | 1610700 A2 | 1/2006 |
| IN | 2761DELNP2012 A | 9/2015 |
| JP | 2003509107 A | 3/2003 |

(56) References Cited

FOREIGN PATENT DOCUMENTS

| | | |
|---|---|---|
| JP | 2003523242 A | 8/2003 |
| JP | 2007501055 A | 1/2007 |
| JP | 2007515990 A | 6/2007 |
| JP | 2009521291 A | 6/2009 |
| JP | 2009530052 A | 8/2009 |
| JP | 2013505071 | 2/2013 |
| JP | 6077069 B2 | 1/2017 |
| JP | 2017530749 A | 10/2017 |
| WO | WO-2001054601 A1 | 8/2001 |
| WO | WO-2001062136 A2 | 8/2001 |
| WO | WO-2002096309 A1 | 12/2002 |
| WO | WO-2007014192 A2 | 2/2007 |
| WO | WO-2007103376 A2 | 9/2007 |
| WO | WO-2009023666 A2 | 2/2009 |
| WO | WO-2009058960 A2 | 5/2009 |
| WO | WO-2009102985 A2 | 8/2009 |
| WO | WO-2011035103 A2 | 3/2011 |
| WO | WO-2011035103 A3 | 3/2011 |
| WO | 2013102103 | 7/2013 |
| WO | WO-2016033311 A1 | 3/2016 |

OTHER PUBLICATIONS

International Search Report dated May 11, 2011; International Application No. PCT/US2010/049247.
"U.S. Appl. No. 12/884,242, 312 Amendment filed Feb. 14, 2014", 3 pgs.
"U.S. Appl. No. 12/884,242, Advisory Action dated Jul. 23, 2013", 6 pgs.
"U.S. Appl. No. 12/884,242, Advisory Action dated Sep. 6, 2013", 3 pgs.
"U.S. Appl. No. 12/884,242, Application filed Sep. 17, 2010", 62 pgs.
"U.S. Appl. No. 12/884,242, Examiner Interview Summary dated Aug. 20, 2012", 3 pgs.
"U.S. Appl. No. 12/884,242, Final Office Action dated Mar. 14, 2013", 19 pgs.
"U.S. Appl. No. 12/884,242, Non Final Office Action dated Aug. 31, 2012", 13 pgs.
"U.S. Appl. No. 12/884,242, Notice of Allowance dated Nov. 15, 2013", 14 pgs.
"U.S. Appl. No. 12/884,242, Response filed Jul. 15, 2013 to Final Office Action dated Mar. 14, 2013", 15 pgs.
"U.S. Appl. No. 12/884,242, Response filed Jul. 26, 2013 to Advisory Action dated Jul. 23, 2013", 10 pgs.
"U.S. Appl. No. 12/884,242, Response filed Aug. 8, 2012 to Restriction Requirement dated Jun. 11, 2012", 8 pgs.
"U.S. Appl. No. 12/884,242, Response filed Nov. 19, 2012 to Non Final Office Action dated Aug. 31, 2012", 13 pgs.
"U.S. Appl. No. 12/884,242, Restriction Requirement dated Jun. 11, 2012", 9 pgs.
"U.S. Appl. No. 12/884,246, 312 Amendment filed May 21, 2013", 4 pgs.
"U.S. Appl. No. 12/884,246, Application filed Sep. 17, 2010", 63 pgs.
"U.S. Appl. No. 12/884,246, Examiner Interview Summary dated Nov. 28, 2012", 4 pgs.
"U.S. Appl. No. 12/884,246, Final Office Action dated Oct. 15, 2012", 30 pgs.
"U.S. Appl. No. 12/884,246, Non Final Office Action dated Jun. 7, 2012", 18 pgs.
"U.S. Appl. No. 12/884,246, Notice of Allowance dated Mar. 26, 2013", 14 pgs.
"U.S. Appl. No. 12/884,246, PTO Response to Rule 312 Communication dated Jun. 4, 2013", 2 pgs.
"U.S. Appl. No. 12/884,246, Response filed Sep. 5, 2012 to Non Final Office Action dated Jun. 7, 2012", 18 pgs.
"U.S. Appl. No. 12/884,246, Response filed Dec. 5, 2012 to Final Office Action dated Oct. 15, 2012", 19 pgs.
"U.S. Appl. No. 14/230,548, Examiner Interview Summary dated Feb. 4, 2015", 3 pgs.
"U.S. Appl. No. 14/230,548, Final Office Action dated May 1, 2015", 16 pgs.
"U.S. Appl. No. 14/230,548, Non Final Office Action dated Nov. 5, 2015", 15 pgs.
"U.S. Appl. No. 14/230,548, Non Final Office Action dated Nov. 6, 2014", 10 pgs.
"U.S. Appl. No. 14/230,548, Preliminary Amendment filed Aug. 29, 2014", 4 pgs.
"U.S. Appl. No. 14/230,548, Response filed Jan. 26, 2015 to Non Final Office Action dated Nov. 6, 2014", 9 pgs.
"U.S. Appl. No. 14/230,548, Response filed Feb. 3, 2016 to Non Final Office Action dated Nov. 5, 2015", 7 pgs.
"U.S. Appl. No. 14/230,548, Response filed Aug. 3, 2015 to Final Office Action dated May 1, 2015", 7 pgs.
"Australian Application Serial No. 2010295518, Office Action dated Sep. 8, 2014", 4 pgs.
"Australian Application Serial No. 2010295518, Subsequent Examiners Report dated Feb. 1, 2016", 3 pgs.
"European Application Serial No. 10766149.8, Decision of Grant dated Jun. 5, 2015", 2 pgs.
"European Application Serial No. 10766149.8, Examination Notification Art. 94(3) dated Dec. 12, 2013", 5 pgs.
"European Application Serial No. 10766149.8, Office Action dated May 11, 2012", 2 pgs.
"European Application Serial No. 10766149.8, Response filed Apr. 10, 2014 to Examination Notification Art. 94(3) dated Dec. 12, 2013", 24 pgs.
"European Application Serial No. 10766149.8, Response filed Nov. 15, 2012 to Office Action dated May 11, 2012", 22 pgs.
"European Application Serial No. 15174047.9, Office Action dated Aug. 14, 2015", 1 pg.
"International Application Serial No. PCT/US2010/049247, International Preliminary Report on Patentability dated Mar. 29, 2012", 9 pgs.
"International Application Serial No. PCT/US2010/049247, Written Opinion dated May 11, 2011", 7 pgs.
"International Application Serial No. PCT/US2015/047157, International Search Report dated Dec. 7, 2015", 5 pgs.
"International Application Serial No. PCT/US2015/047157, Written Opinion dated Dec. 7, 2015", 7 pgs.
"Japanese Application Serial No. 2012-529924, Non Final Office Action dated Apr. 22, 2014", W/ English Translation, 5 pgs.
"Japanese Application Serial No. 2012-529924, Preliminary Amendment filed Jul. 30, 2015", W/ English Claims, 8 pgs.
"Japanese Application Serial No. 2012-529924, Response filed Oct. 20, 2014 Non Final Office Action dated Apr. 22, 2014", W/ English Claims, 6 pgs.
"U.S. Appl. No. 14/230,548, Non Final Office Action dated Oct. 7, 2016", 7 pgs.
"Japanese Application Serial No. 2015-150885, Office Action dated Aug. 16, 2016", (W/ English Translation), 4 pgs.
"U.S. Appl. No. 12/884,246, Advisory Action dated Jan. 3, 2013", 3 pgs.
"U.S. Appl. No. 14/230,548, Final Office Action dated May 13, 2016", 17 pgs.
"U.S. Appl. No. 14/230,548, Response filed Aug. 15, 2016 to Final Office Action dated May 13, 2016", 7 pgs.
"Australian Application Serial No. 2010295518, Response filed May 6, 2016 to Subsequent Examiners Report dated Feb. 1, 2016", 13 pgs.
"Canadian Application Serial No. 2,774,688, Office Action dated Jun. 1, 2016", 3 pgs.
"European Application Serial No. 15174047.9, Extended European Search Report dated Feb. 8, 2016", 11 pgs.
"European Application Serial No. 15174047.9, Partial European Search Report dated Oct. 20, 2015", 7 pgs.
"U.S. Appl. No. 14/230,548, Notice of Allowance dated May 5, 2017", 8 pgs.
"U.S. Appl. No. 14/230,548, Response filed Jan. 9, 2017 to Non Final Office Action dated Oct. 7, 2016", 7 pgs.

(56) References Cited

OTHER PUBLICATIONS

"Australian Application Serial No. 2015308881, First Examination Report dated Dec. 13, 2018", 3 pgs.
"Australian Application Serial No. 2016219567, First Examination Report dated May 2, 2018", 2 pgs.
"Canadian Application Serial No. 2,774,688, Office Action dated Mar. 21, 2017", 3 pgs.
"Canadian Application Serial No. 2,774,688, Office Action dated Dec. 27, 2017", 4 pgs.
"Canadian Application Serial No. 2,774,688, Response filed Jun. 18, 2018 to Office Action dated Dec. 27, 2017", 5 pgs.
"Canadian Application Serial No. 2,774,688, Response filed Sep. 25, 2017 to Office Action dated Mar. 21, 2017", 6pgs.
"Canadian Application Serial No. 2,774,688, Response filed Dec. 1, 2016 to Office Action dated Jun. 1, 2016", 5 pgs.
"Chinese Application Serial No. 201580057117.6, Office Action dated Dec. 11, 2018", (W/ English Translation), 16 pgs.
"European Application Serial No. 15174047.9, Office Action dated Feb. 22, 2017", 6 pgs.
"European Application Serial No. 15174047.9, Response filed Jul. 4, 2017 to Office Action dated Feb. 22, 2017", 11 pgs.
"European Application Serial No. 15760351.5, Response filed Oct. 23, 2017 to Office Action dated Apr. 11, 2017", 16 pgs.
"Indian Application Serial No. 2761DELNP2012; First Examination Report dated Feb. 13, 2019", (W/ English Translation), 5 pgs.
"International Application Serial No. PCT/US2015/047157, International Preliminary Report on Patentability dated Mar. 9, 2017", 9 pgs.
"Japanese Application Serial No. 2015-150885, Response filed Nov. 16, 2016 to Office Action dated Aug. 16, 2016", (English Translation of Claims), 6 pgs.
"Japanese Application Serial No. 2017-002689, Office Action dated Oct. 24, 2017", (W/ English Translation), 4 pgs.
"Japanese Application Serial No. 2017-002689, Response Filed Jan. 12, 2018 to Office Action dated Oct. 24, 2017", (W/ English Translation of Claims), 6 pgs.
"Chinese Application Serial No. 201580057117.6, Response Filed Mar. 14, 2019 to Office Action dated Dec. 11, 2018", w English Claims, 9.
"Japanese Application Serial No. 2017-511587, Office Action dated May 7, 2019", w English translation, 8 pgs.

* cited by examiner

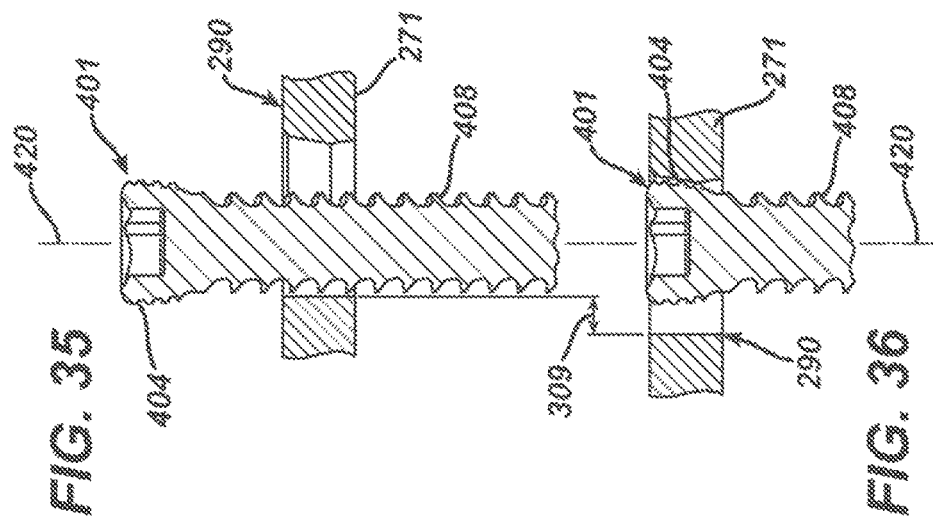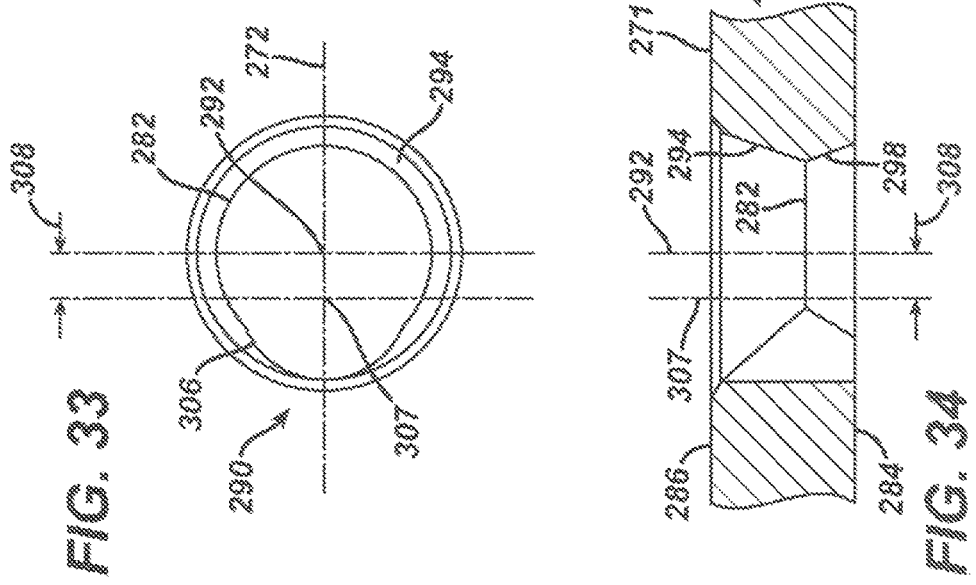

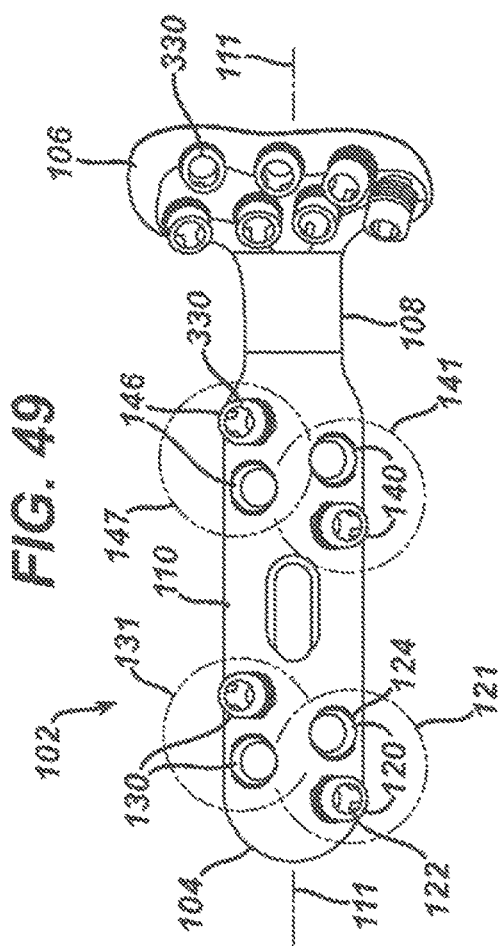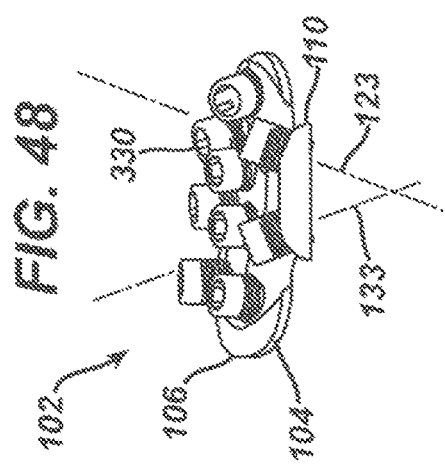

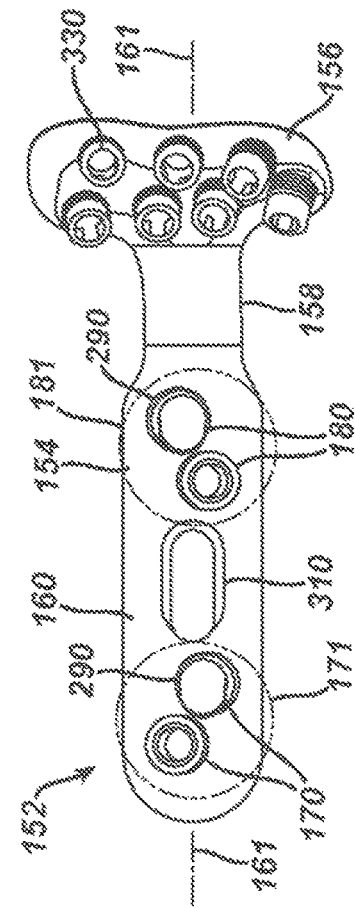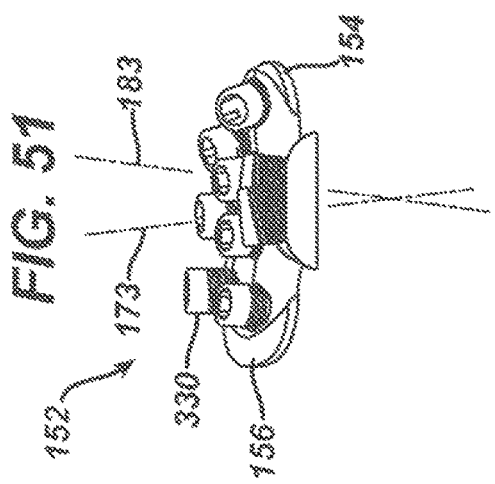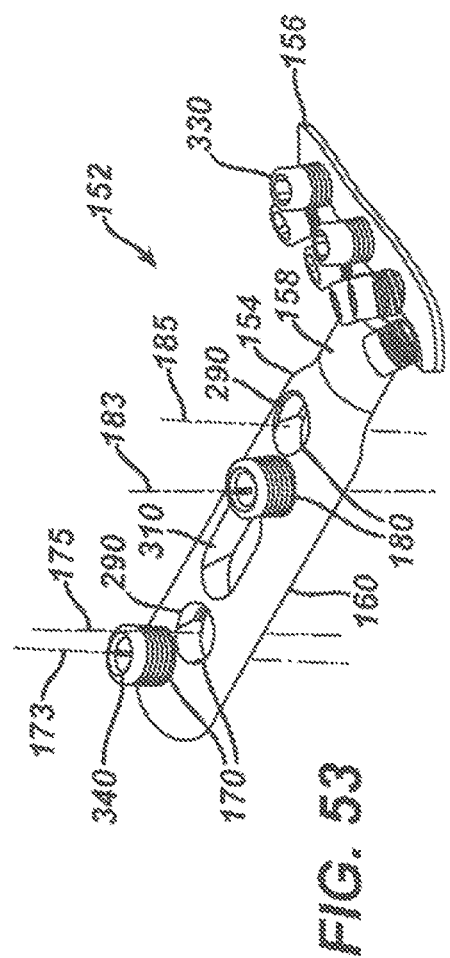

BONE PLATE SYSTEM AND METHOD

CROSS-REFERENCE TO RELATED APPLICATIONS

This application is a continuation-in-part of Ser. No. 14/230,548 filed on Mar. 31, 2014, which is a divisional of U.S. patent application Ser. No. 12/884,242 filed on Sep. 17, 2010, now U.S. Pat. No. 8,685,068, which claims the benefit of U.S. Provisional Application No. 61/243,752 filed on Sep. 18, 2009. The entire disclosure of each of the above applications is incorporated herein by reference.

BACKGROUND

This section provides background information related to the present disclosure which is not necessarily prior art.

This disclosure relates generally to surgical devices and procedures, and more particularly, to orthopaedic surgical devices and procedures for the internal fixation of fractured bones.

Bone plate systems for the internal fixation of fractured bones of patients are typically provided by manufacturers in non-sterile, reusable trays to the surgical care facilities. These trays may include a number of bone plates of various types, sizes and shapes for various patient anatomies and surgical indications. The trays also may include a number of reusable instruments and a large number of bone plate fasteners of numerous sizes and types, many more than what would normally be required for any given patient and surgical indication. Prior to the surgical procedure, the surgical care facility personnel must be sure that a complete tray of these components is assembled and sterilized, such as by steam autoclave. Often a manufacturer's sales representative may be present at the facility to assist in assembling the tray of necessary components in preparation for the surgical procedure. After the procedure is completed, the tray of unused components may be sterilized and stored for a later surgical procedure. Any components missing from the tray generally are replenished and the entire tray is sterilized again prior to a surgical procedure for another patient.

The overall cost of providing to the surgeon many more components in sterile condition than would normally be required for a particular patient with a specific surgical indication can be significant. This overall cost may include costs related to the necessary inventory of bone plate system components, repeated sterilization of the components, the need to make high quality, durable instruments for repeated use, the assistance of manufacturers' representatives, and other factors. Such factors may also impact the availability of such bone plate systems to trauma surgeons practicing in certain areas of the world.

SUMMARY

This section provides a general summary of the disclosure, and is not a comprehensive disclosure of its full scope or all of its features.

In one aspect, the present disclosure provides a bone plate system for the internal fixation of a fractured bone of a patient. The system includes a bone plate including a head portion and a shaft portion having a longitudinal axis. The head portion may be wider than the shaft portion. The bone plate further includes a plurality of threaded, locking bone fastener apertures defined in the shaft portion, and a plurality of non-threaded, non-locking bone fastener apertures defined in the shaft portion and aligned on the longitudinal axis. Each of the plurality of non-threaded apertures may be paired together with at least one of the plurality of the threaded apertures to form a plurality of discrete aperture clusters, wherein a first aperture cluster is positioned about a proximal end of the shaft portion, and a second aperture cluster is positioned about a distal end of the shaft portion. The system may include a plurality of bone fasteners, each bone fastener comprising a shaft and a head. Each head may be dimensioned and configured to threadedly engage the threaded, locking bone fastener apertures to provide a fixed angle locking construct. Each head may also be dimensioned and configured to directly engage the non-threaded, non-locking bone fastener apertures to provide a polyaxial compressive construct.

In another aspect, the present disclosure provides a method for implanting a bone plate system for the internal fixation of a fractured bone of a patient. The method includes providing a bone plate including a head portion and a shaft portion. The shaft portion has a longitudinal axis and comprises a plurality of discrete aperture clusters, each aperture cluster including a non-threaded, non-locking bone fastener aperture configured to provide a polyaxial non-locking compressive construct and at least one threaded, locking bone fastener aperture. The method includes aligning the bone plate with the bone. Once aligned, a first bone fastener may be inserted into the bone through at least one of the non-threaded bone fastener apertures in a direction normal to the longitudinal axis, dynamically compressing the bone along the longitudinal axis of the shaft portion of the bone plate. A second bone fastener may be inserted into the bone through at least one of the threaded, locking bone fastener apertures in a direction oblique to the longitudinal axis and securing the bone plate to the bone.

In yet another aspect, the method includes providing a bone plate including a head portion and a shaft portion, the shaft portion having a longitudinal axis and comprising a pair of discrete aperture clusters and a unidirectionally ramped aperture aligned with the longitudinal axis and disposed between the pair of aperture clusters. Each aperture cluster may include a non-threaded, non-locking bone fastener aperture configured to provide a polyaxial compressive construct and at least one threaded, locking bone fastener aperture. Once the bone plate is aligned with the bone, the method includes shaping the bone plate with the bone. The shaping may include inserting a first bone fastener into the bone through at least one of the unidirectionally ramped aperture and non-threaded bone fastener apertures in a direction normal to the longitudinal axis, and dynamically compressing the bone along the longitudinal axis of the shaft portion of the bone plate. The bone plate is then secured to the bone, which may include inserting a second bone fastener into the bone through at least one of the threaded, locking bone fastener apertures in a direction oblique to the longitudinal axis and locking the bone plate to the bone.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 33 is a top view of a unidirectionally ramped aperture;

FIG. 34 is a cross-sectional view of the unidirectionally ramped aperture of FIG. 33;

FIG. 35 is a cross-sectional view of the unidirectionally ramped aperture of FIG. 34 with the first fastener of FIG. 20 partially inserted therein;

FIG. 36 is a cross-sectional view of the unidirectionally ramped aperture of FIG. 35 with the first fastener of FIG. 20 fully inserted therein;

FIG. 48 is an end view of a first DVR assembly;

FIG. 49 is a top view of the first DVR assembly of FIG. 48;

FIG. 50 is a perspective view of the first DVR assembly of FIG. 48;

FIG. 51 is an end view of a second DVR assembly;

FIG. 52 is a top view of the second DVR assembly of FIG. 51;

FIG. 53 is a perspective view of the second DVR assembly of FIG. 51;

Corresponding reference numerals indicate corresponding parts throughout the several views of the drawings.

DETAILED DESCRIPTION

Figure 1:
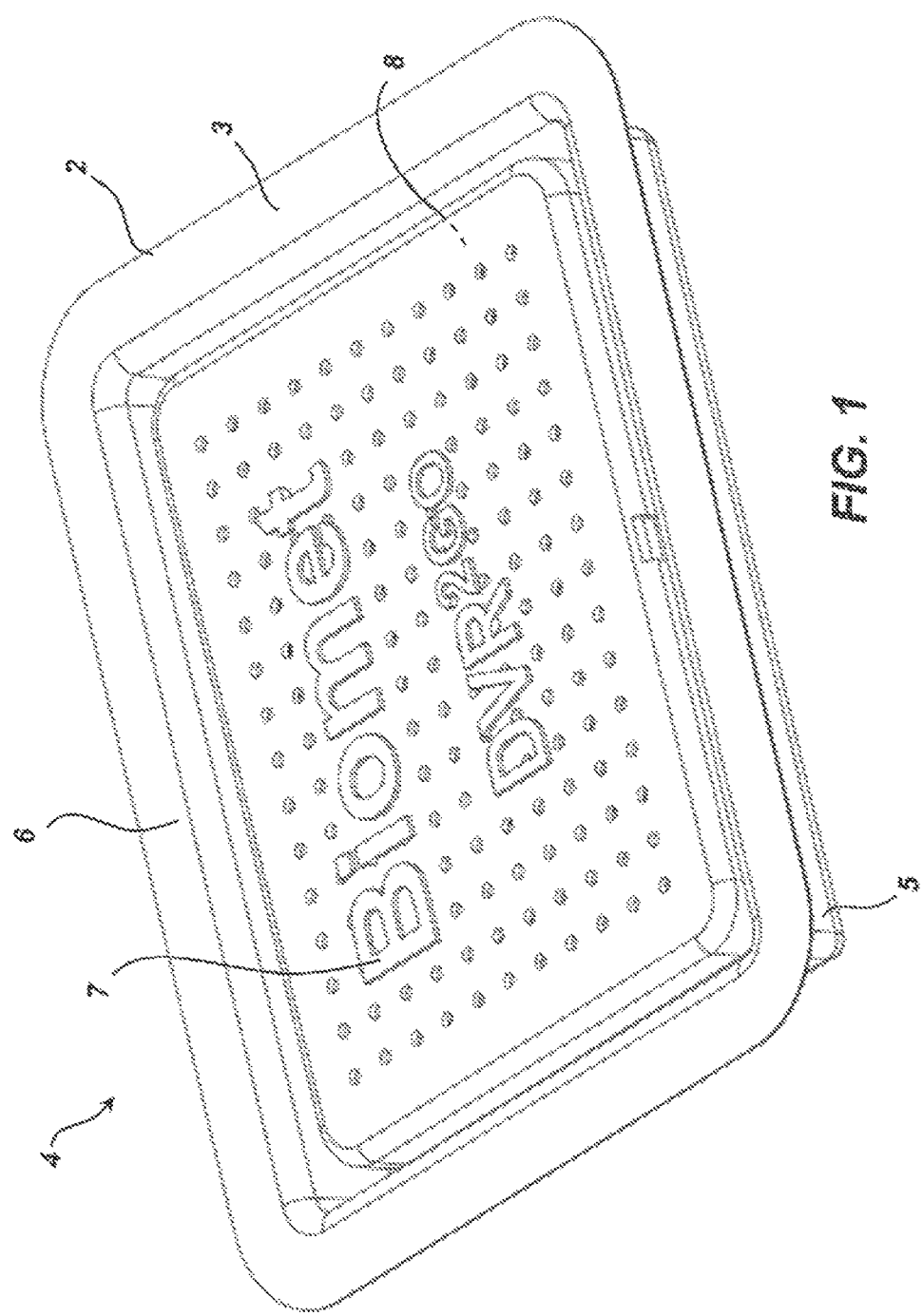
FIG. 1 is a top perspective view of a single-use, orthopaedic surgery kit (or more simply, a single-use kit), showing a first embodiment of a container sealed inside of an outer package.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Throughout the following description, the term "user" may refer to the surgeon or other users of the single-use kit, including surgical assistants, technicians, and so on. Also, the term "single-use", as used herein, is interchangeable with the terms "disposable" or "disposable, single-indication", meaning that the kit, including all the components contained therein, is intended for use for only one surgical patient. After completion of the surgical procedure, the components that are not implanted into the patient may be discarded using conventional methods. However, for some embodiments, it is also possible that the single-use kit or a portion of it can be resterilized for use in a surgical procedure for another patient.

Each single-use kit is designed for transport from the manufacturer to the surgical care facility, storage, and then finally, sterile presentation to the surgeon for use during the surgical procedure. Using the appropriate single-use kit for a particular surgical procedure may reduce the need for the surgical care facility to maintain a large inventory of individual components that must be combined into a surgical tray and sterilized prior to that procedure. Furthermore, using the appropriate single-use kit may reduce the need for special assistance from the representatives of the component manufacturers, and assures the surgeon that the components are always new and in sterile condition. In addition, since the single-use kit may be designated to have a single product code, expensing the cost of the kit to the patient and/or the patient's health care provider may be simplified and result in reduced overhead costs for the surgical procedure.

We envision that occasionally the surgeon may select a single-use kit containing components for a particular type of bone fracture procedure, and then determine during the surgical procedure that the single-use kit is not appropriate for that patient. In case a single-use kit is contaminated during (or prior to) a surgical procedure for a patient and then is not used for that patient, it is possible to steam autoclave the kit with the components contained therein, such that the kit may be used in a surgical procedure for a different patient.

One advantage of these single-use kit embodiments is the commonality of components that is possible due to the reduction of the number of bone plate fastener types required, as compared to currently available systems for similar surgical procedures. By minimizing the variety of required fastener types for attaching a plurality of different types of bone plates, an economy is realized in the instrumentation required to perform the various surgical procedures. As a consequence, the size and cost of the single-use kit is minimized. We envision that this may increase availability of such kits to surgical care centers throughout the world, so that more trauma patients may be treated using the latest implants, instruments and techniques. In addition, we envision that the overall surgical procedure may be simplified, potentially resulting in reduced surgical procedure duration and improved clinical outcome for the patient.

Referring now to the figures, FIG. 1 is a top perspective view of a single-use kit 4, which includes a container 8 according to a first embodiment, a plurality of components (not visible) contained therein, and an outer package 2. (Each of the plurality of components will be later described in detail for each of the single-use kit embodiments disclosed herein.) Outer package 2 physically protects container 8 and the components contained therein, and may also serve to seal and to maintain the sterility of container 8 and the components contained therein until accessed prior to or during the surgical procedure.

Outer package 2 may be formed from materials and by methods that are well known in the art for the sterile packaging of medical devices. Outer package 2 includes a pan 5 that is sized and shaped to hold container 8. Pan 5 has a peripheral lip 3 and may be formed from a plastic material suitable for maintaining sterility. Outer package 2 may include a removably attachable, sealing membrane 6 that is adhered to peripheral lip 3 of pan 5 prior to sterilization by gamma radiation or other sterilization methods known in the art. The user peels sealing membrane 6 from pan 5 to access container 8. Sealing membrane 6 may be formed from a suitable, transparent plastic material so that a graphic 20 displayed on container 8 is visible prior to opening outer package 2. Graphic 20 may provide information pertaining to, for example, the manufacturer, the distributor, the surgical indications, the product code(s), the components contained therein, the overall physical characteristics (i.e., size and weight), the relevant patents, warnings, directions for opening, and so on. Alternatively, sealing membrane 6 may be formed from a suitable, solidly colored or translucent plastic material, and may include a graphic that is similar or complementary to graphic 20

It should be understood that other embodiments of single-use kit 4 may not include outer package 2 at all or that outer package 2 may provide only non-sterile protection for container 8 and the components contained therein. For example, container 8 and the components contained therein may be first removed from outer package 2 in a non-sterile condition and then sterilized at the surgical care facility prior to the surgical procedure.

Figure 2:
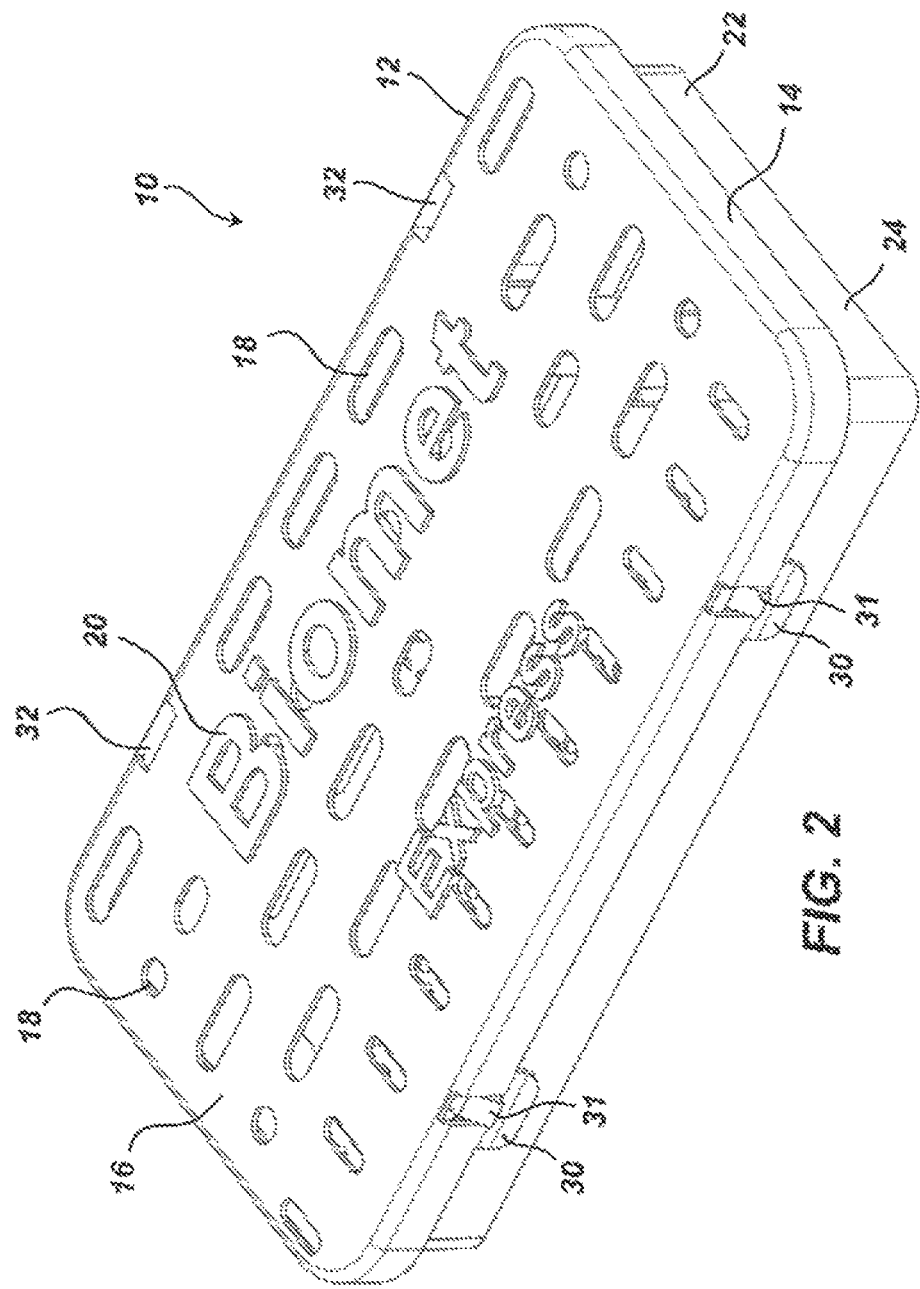
FIG. 2 is a top perspective view of an alternative embodiment of a container, which includes a bottom tray and a top lid, shown with the lid closed.
Figure 3:
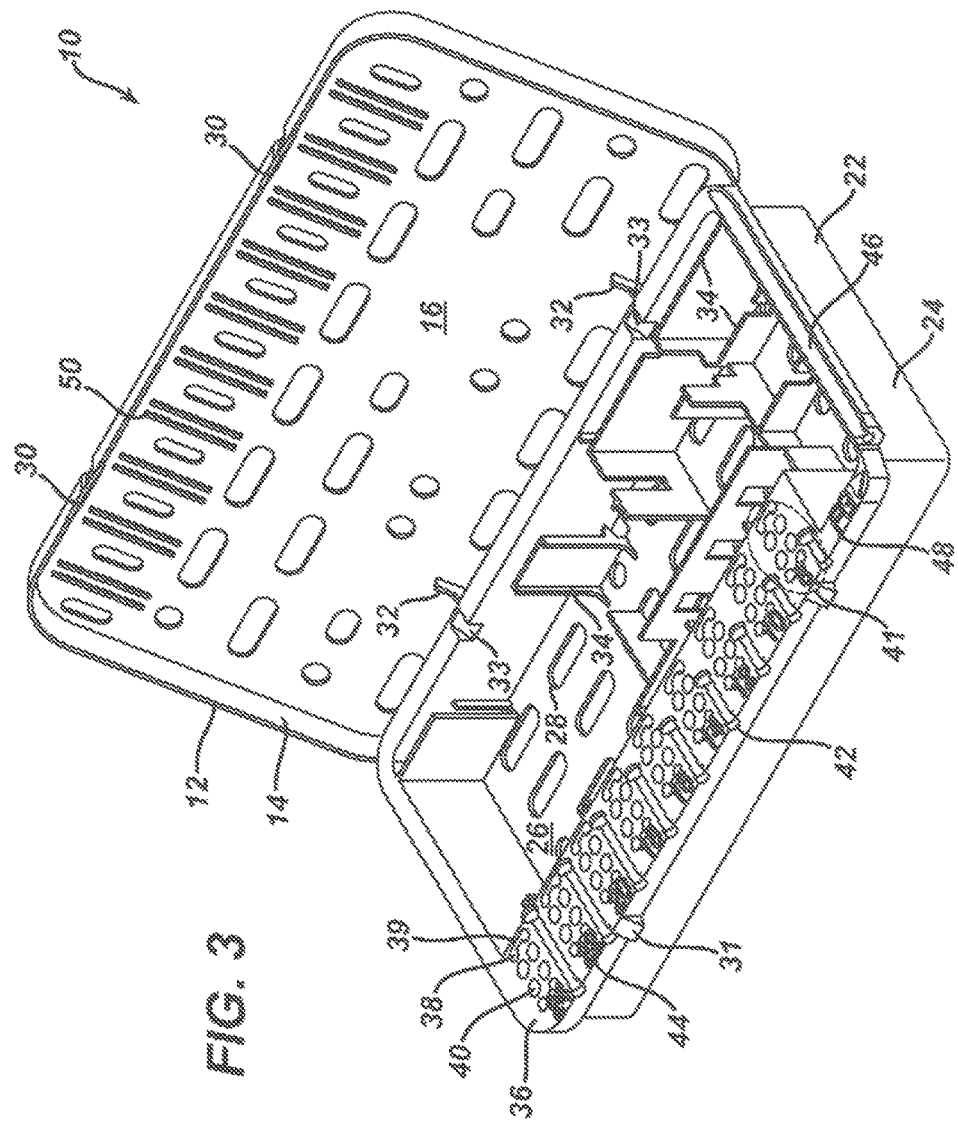
FIG. 3 is a top perspective view of the container of FIG. 2, shown with the lid opened.

FIG. 2 is a top perspective view of a container 10 in a closed configuration according to a second embodiment. FIG. 3 is a top perspective view of container 10 in an open configuration. Container 10 includes a bottom tray 22 and a top lid 12, each of which is formed, such as by injection molding, from any one of a number of polymers, including, for example, polysulfone, polyetherimide and polypropylene. Either one or both of tray 22 and lid 12 may be formed from a transparent polymer to allow viewing of the components contained therein without opening container 10.

Lid 12 may be formed from a polymer that is colored to indicate the surgical indication of the kit or to provide some other type of information to the user. For example, a red color may indicate that the kit is to be used for the right side of the patient's anatomy, a lime color may indicate that the kit is to be used for the left side, and a white color may indicate that the kit is to be used for either side.

As shown in FIGS. 2 and 3, tray 22 has a rectangular shape defined by four tray sides 24, although other shapes may be desirable depending on functional, economic, aesthetic or other reasons. Tray 22 includes a tray bottom 26 that includes a plurality of openings 28 to facility steam access and drainage during sterilization. Lid 12 has a top portion 16 and a peripheral lip 14 that is sized and shaped to fit closely around tray 22. Top portion 16 of lid 12 includes a plurality of openings 18 to facilitate steam sterilization and drainage of container 10 and the components contained therein. Graphic 20 may be integrally molded into top portion 16 of lid 12 and/or selectively highlighted with a suitable ink or paint, such as is well known in the art.

A pair of spaced apart, lid hinge elements 32 is integrally formed on lid 12 for attachment to a pair of spaced apart, tray hinge elements 33 integrally formed on tray 22. Lid 12 may be removably attachable to tray 22 to facilitate access to the components in tray 22 during the surgical procedure, while conserving available space on the surgical stand.

Similarly, a pair of spaced apart, lid latch elements 30, positioned on the opposite side from lid hinge elements 32 of container 10, is integrally formed on lid 12 for attachment to a pair of spaced apart, tray latch elements 31 formed on tray 22. As is well known in the art, many types of lid hinge elements 32, lid latch elements 30, tray hinge elements 33 and tray latch elements 31 are possible.

Figure 4:
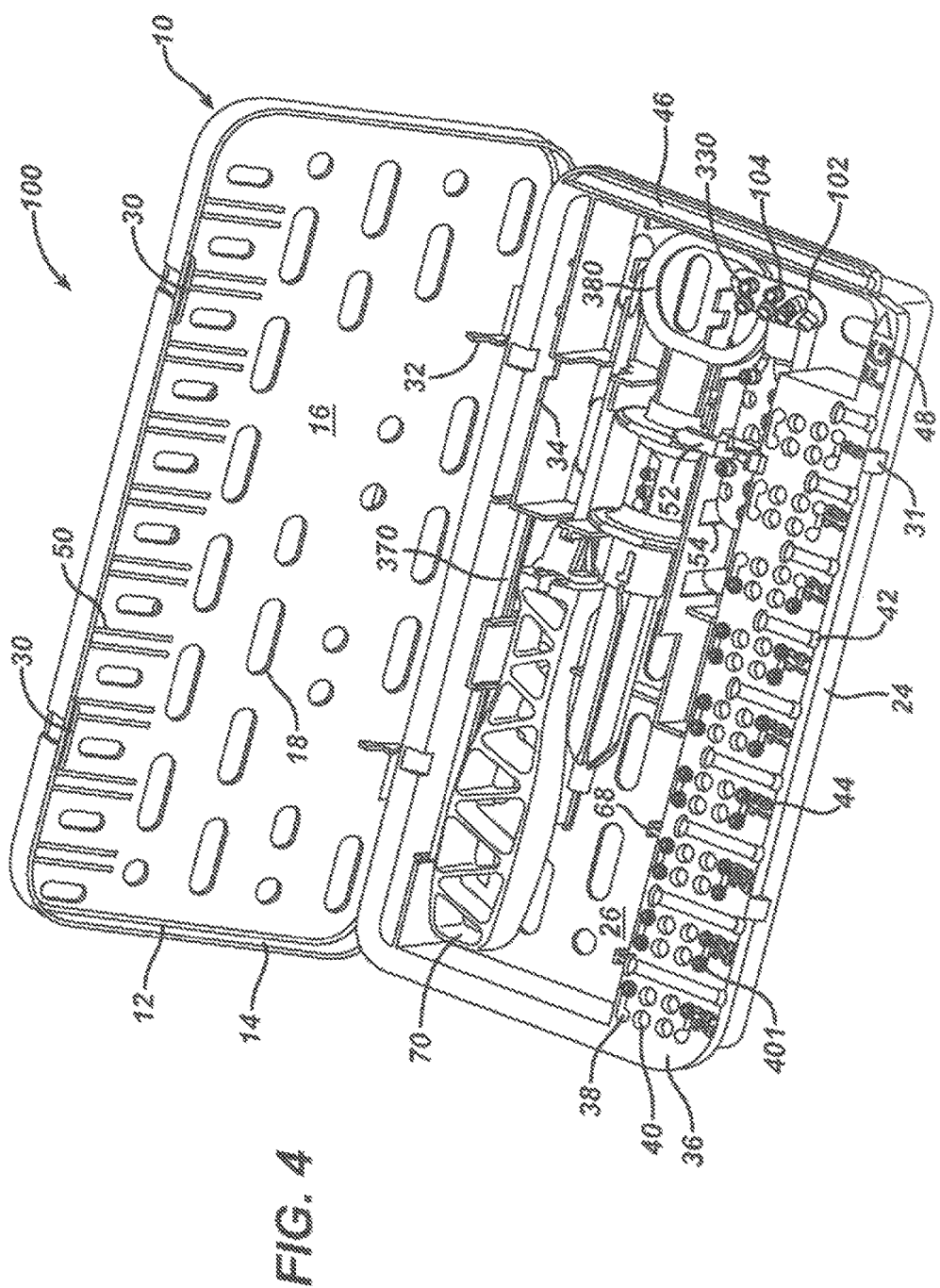
FIG. 4 is a top perspective view of a single-use, distal volar radius (or DVR) kit.

As shown in FIG. 4, tray 22 is compartmentalized by several, integrally formed partitions 34 extending from the inside of tray bottom 26 and the inside of tray sides 24. Tray 22 also includes a shelf 36 that serves as an easily accessible, "screw caddy" for holding a plurality of implantable fasteners, including, for example, a plurality of first fasteners 401 and a plurality of second fasteners 451 (as shown, for example, in FIG. 8). Shelf 36 and partitions 34 are configured to organize and retain the various combinations of all the required components for at least each of the embodiments, as will be described, of the single-use kit embodiments shown herein.

Figure 8:
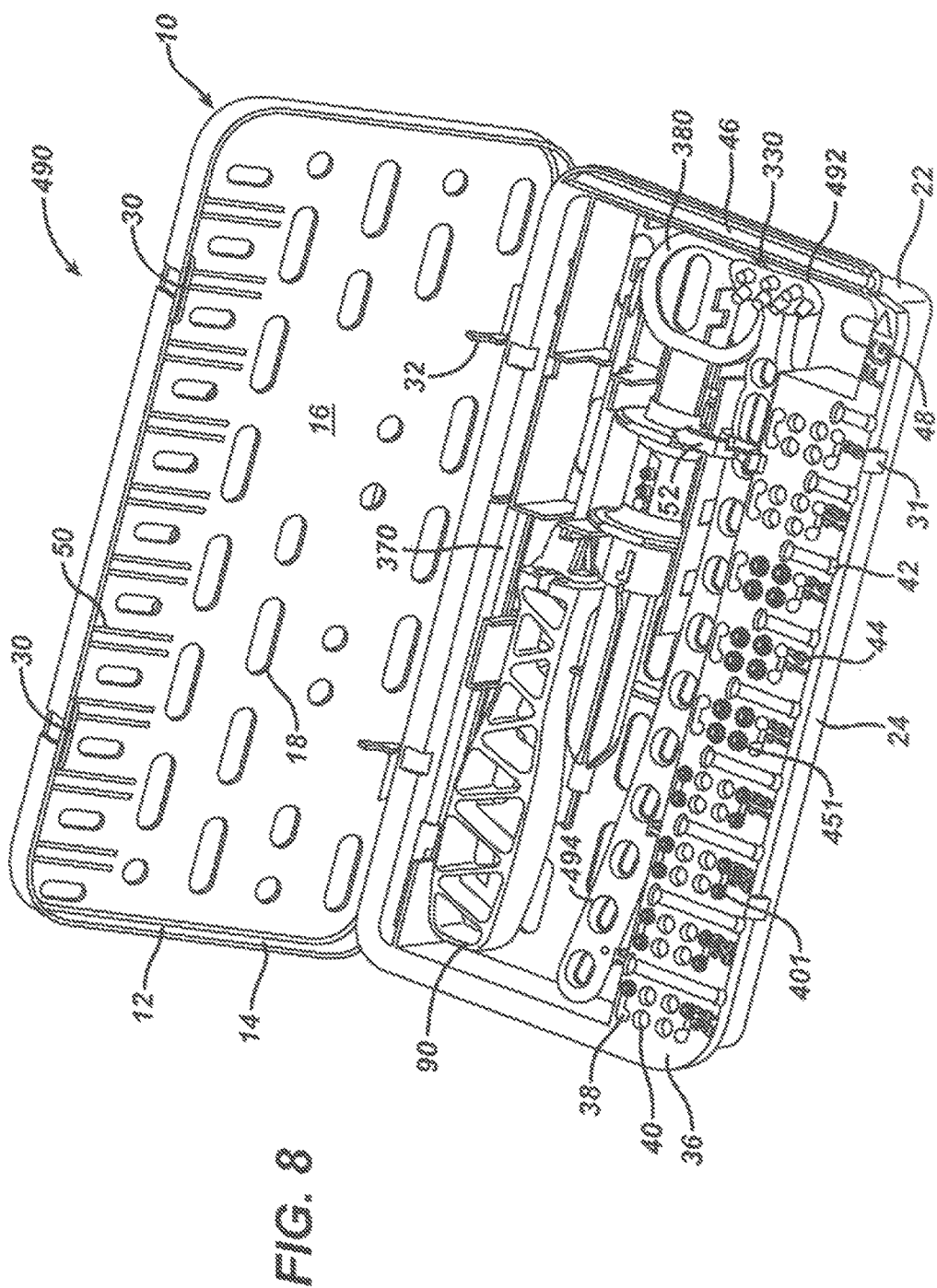
FIG. 8 is a top perspective view of a single-use, DVR long kit.
Figure 9:
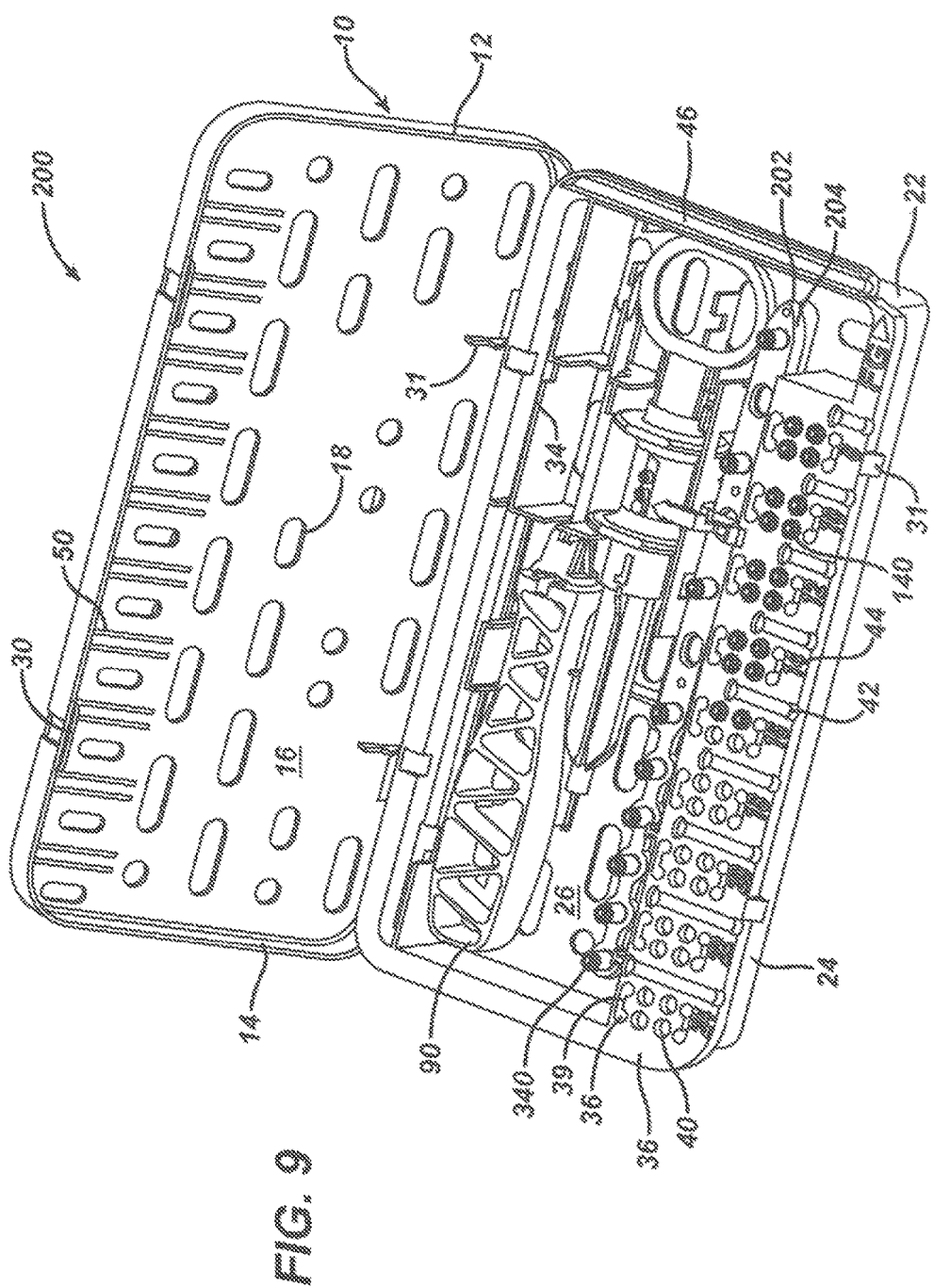
FIG. 9 is a top perspective view of a single-use, fibula kit.
Figure 10:
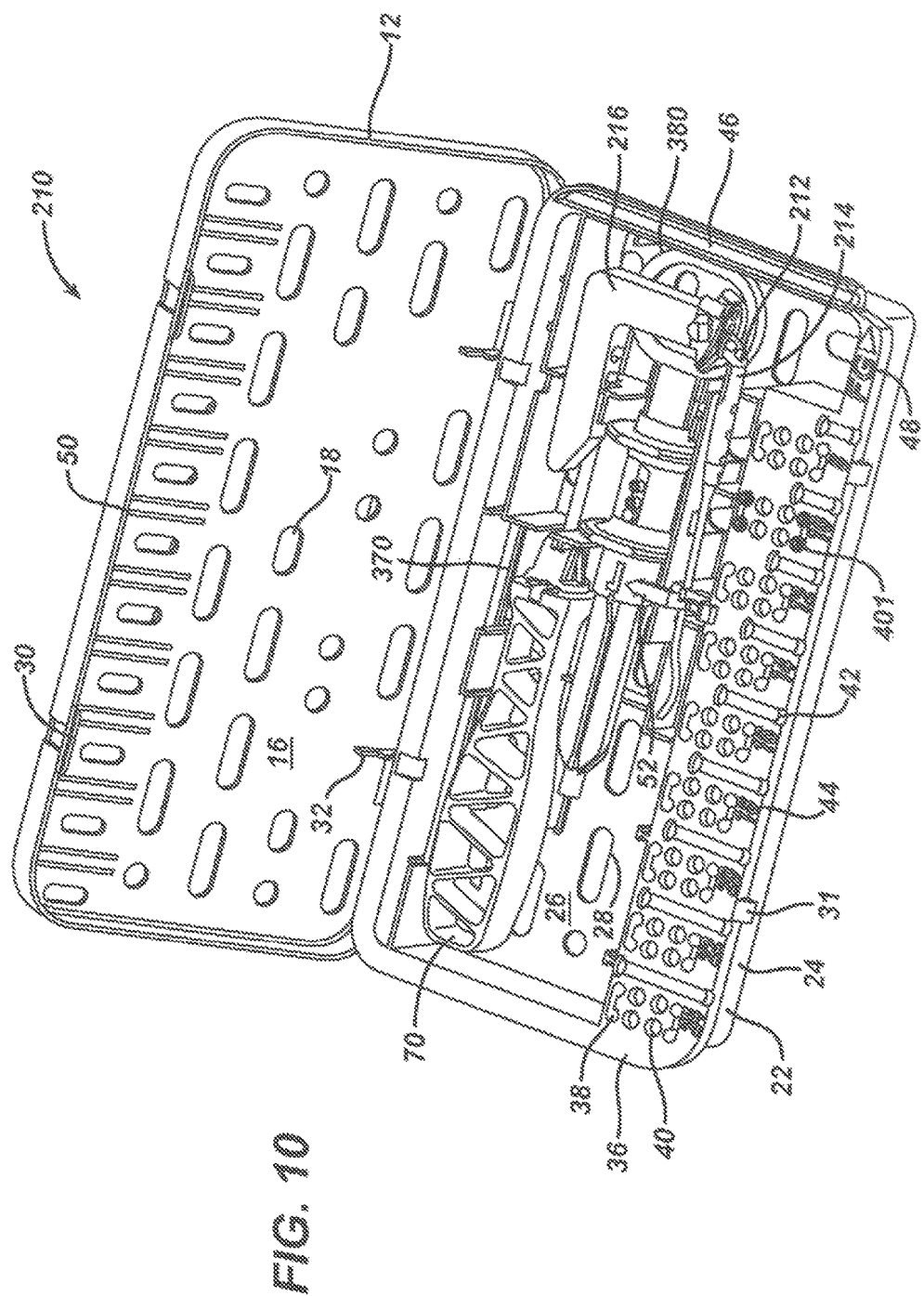
FIG. 10 is a top perspective view of a single-use, dorsal nail plate (or DNP) kit.
Figure 11:
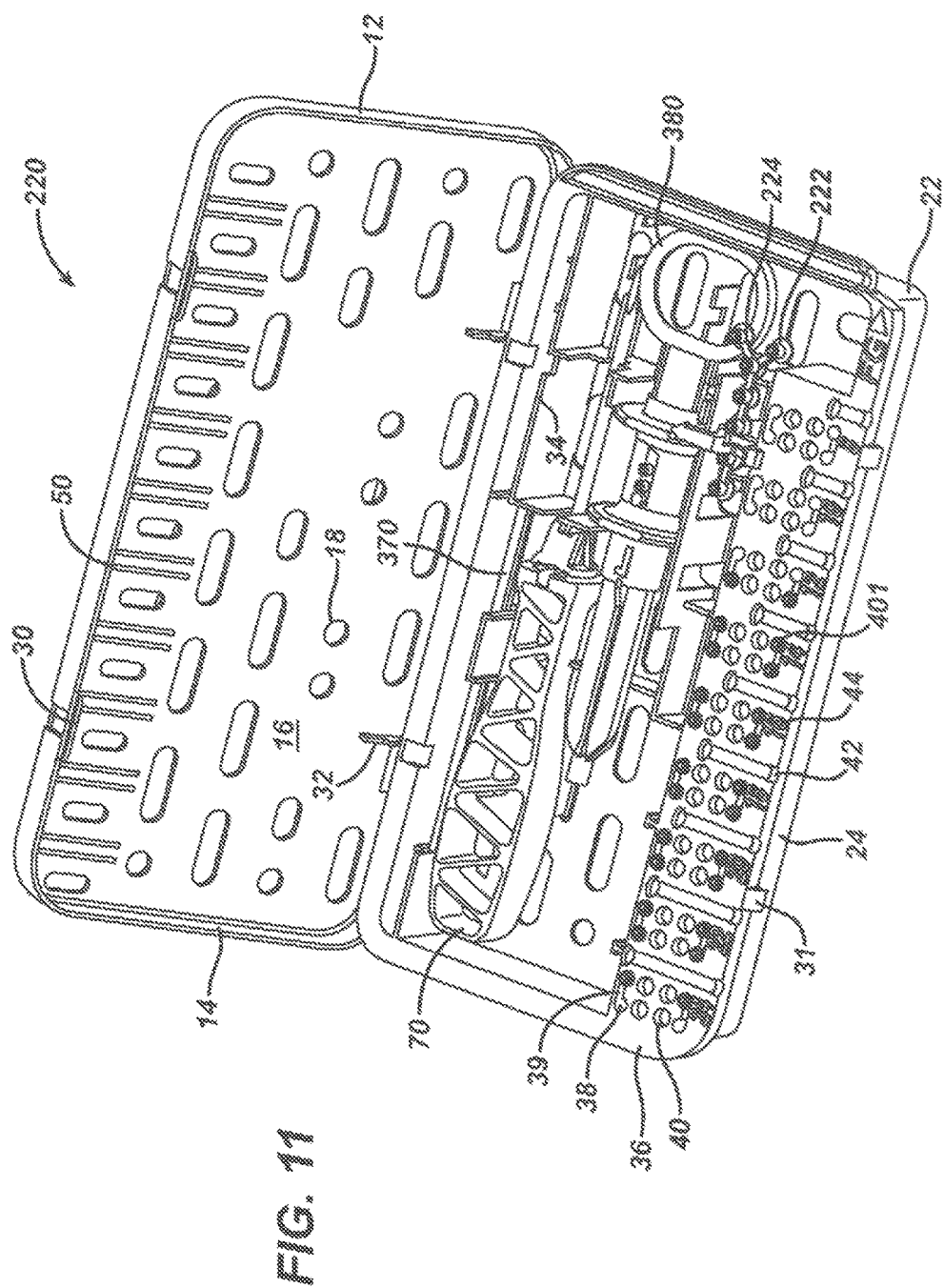
FIG. 11 is a top perspective view of a single-use, flexible fragment fixation (or F3) kit.
Figure 12:
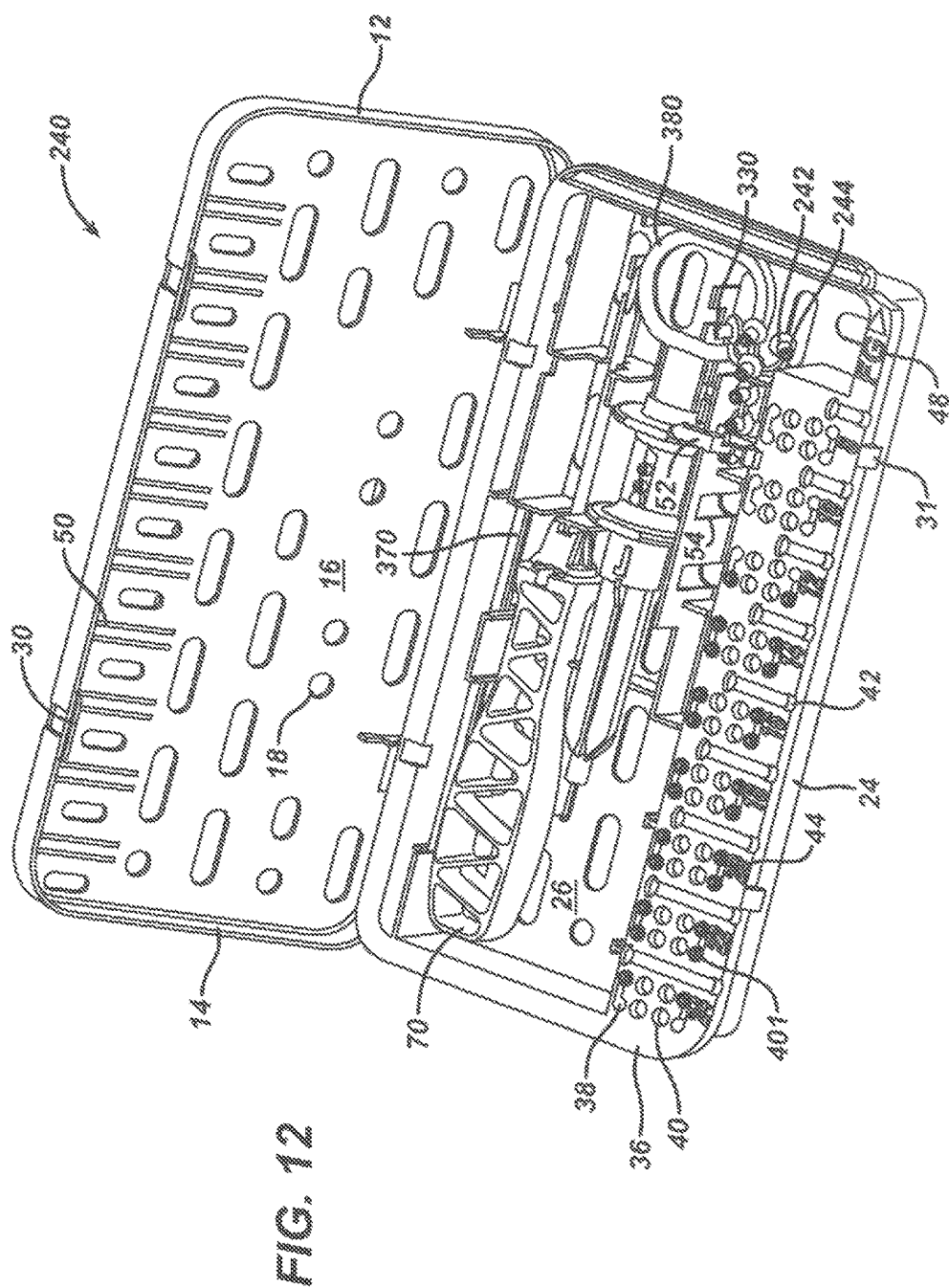
FIG. 12 is a top perspective view of a single-use, proximal radius kit.
Figure 13:
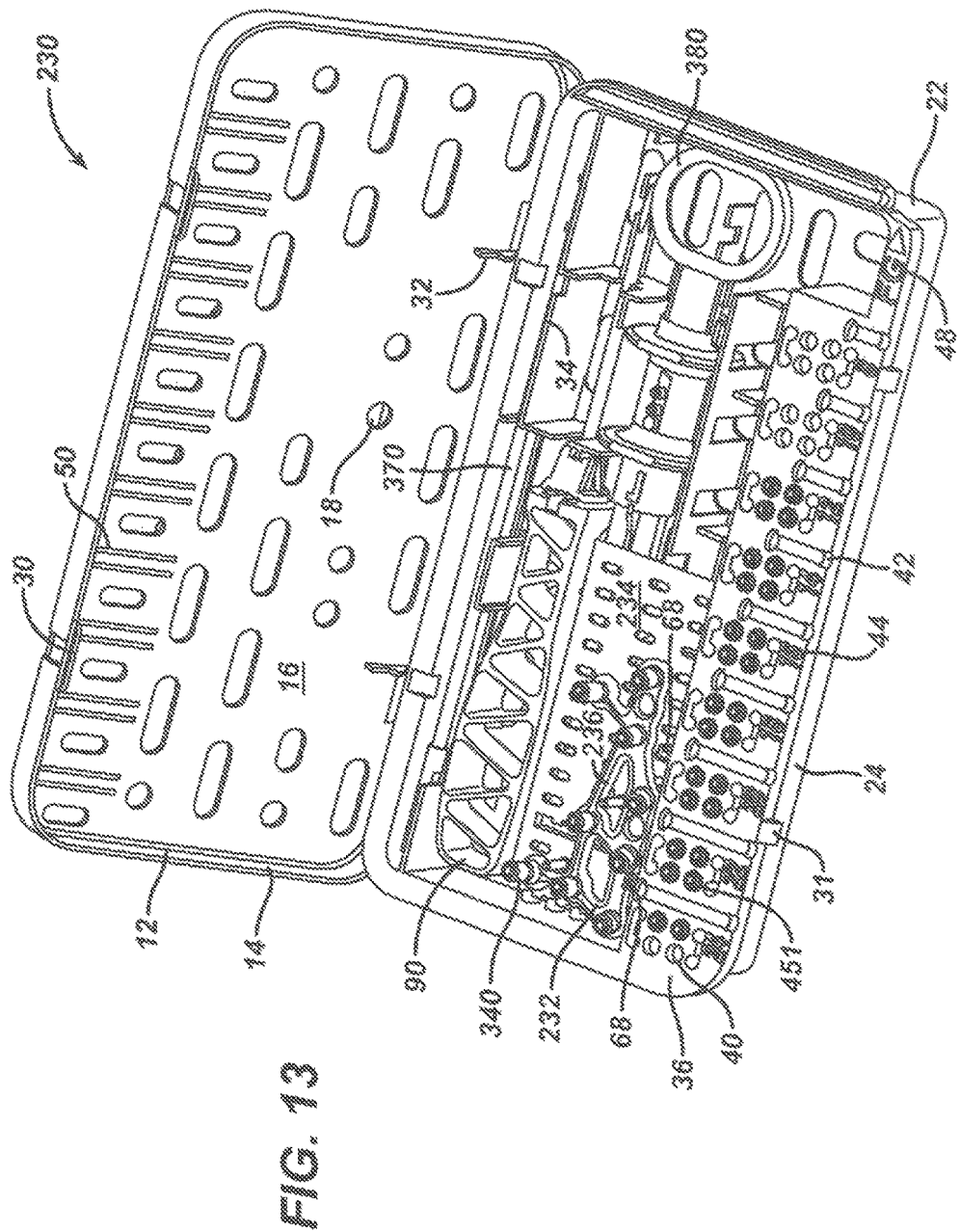
FIG. 13 is a top perspective view of a navicular kit.

Container 10, due to its versatility in design, may be used to contain many different combinations of components, depending on the surgical indication, for at least each of the single-use kit embodiments described herein. FIGS. 4, 8, 9, 10, 11, 12 and 13 show a few of the possible, single-use kit embodiments and may be referenced in combination. Each of these single-use kits is configured for a surgical procedure for the internal fixation of a particular bone of the arm, leg, hand or foot. FIG. 4 shows a distal volar radius kit 100 (or DVR kit 100) for a fracture of the distal radius of the forearm; FIG. 8 shows a single use, DVR Long kit, also for a fracture of the distal radius of the forearm; FIG. 9 shows a single-use, fibula kit for a fracture of the fibula of the lower leg; FIG. 10 shows a single-use, dorsal nail plate kit 210 (or DNP kit 210) for a fracture of the distal radius of the forearm; FIG. 11 shows a single-use, flexible fracture fixation kit 220 (or F3 kit 220) for a fracture of a small bone, such as of the hand or foot; FIG. 12 shows a single-use, proximal radius kit 240 for a fracture of the proximal radius bone at the elbow; FIG. 13 shows a single-use, navicular kit 230 for a fracture of the navicular bone of the foot.

Figure 5:
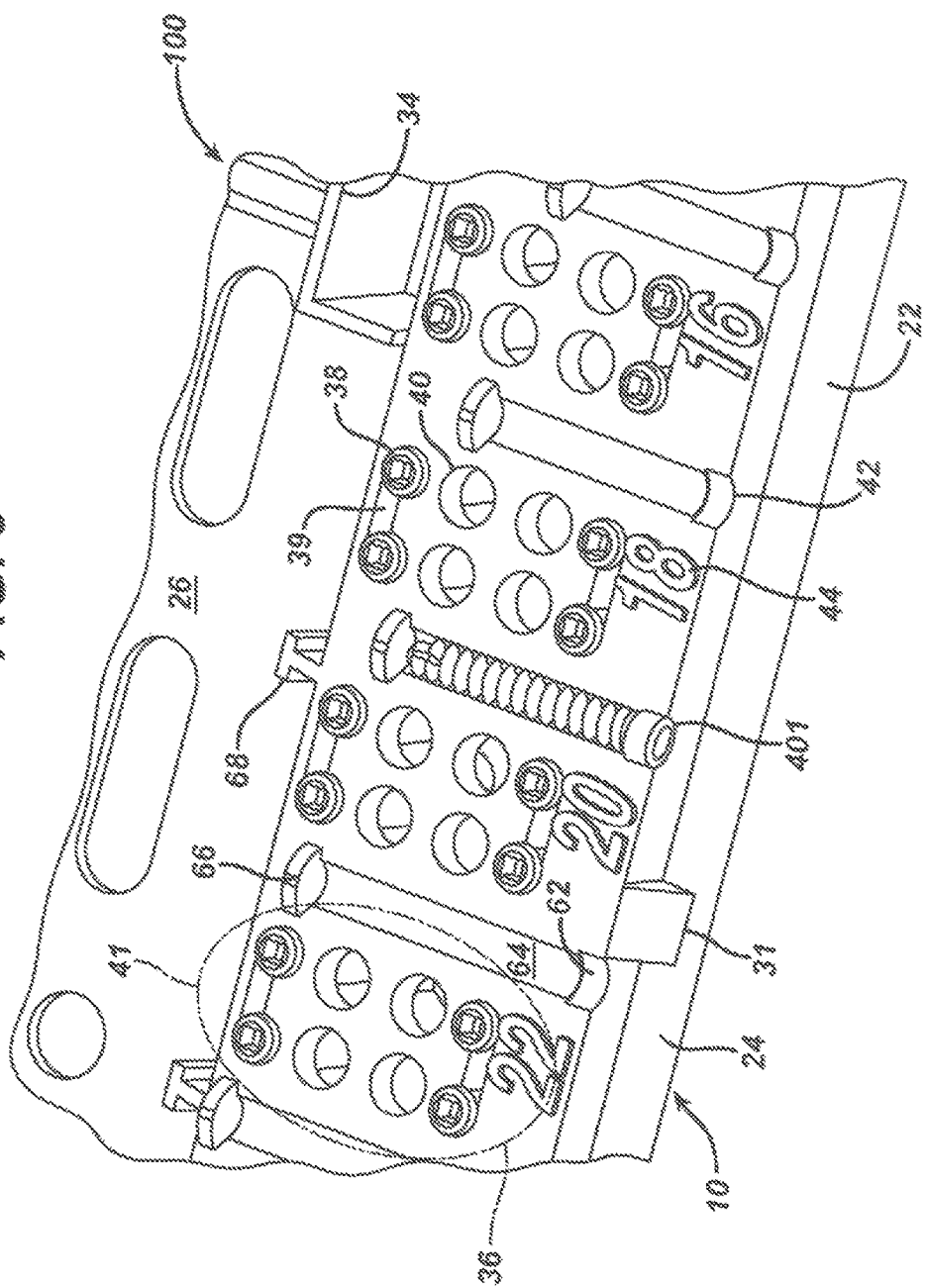
FIG. 5 is a top perspective, detailed view of part of the DVR kit of FIG. 4, showing a first fastener positioned in a fastener length gage.

As shown in FIG. 4 and also in the detailed view of FIG. 5, shelf 36 includes a plurality of first receptacles 38 and a plurality of second receptacles 40. Each of first receptacles 38 is sized and shaped to loosely retain first fastener 401, which has a nominal size, for example, of 2.7 mm, and each of second receptacles 40 is sized and shaped to loosely retain second fastener 451, which has a larger nominal size, for example, of 3.5 mm. First receptacles 38 is integrally formed in lid 12, wherein each pair of first receptacles 38 is connected by a bridge slot 39 to facilitate injection molding. Lid 12 includes a plurality of ribs 50 integrally formed into top portion 16, such that when lid 12 is in a closed position as shown in FIG. 2, each of ribs 50 abuts the exposed end of one of first fasteners 401 and second fasteners 451, such that all of the fasteners are securely retained in container 10.

First fastener receptacles 38 and second fastener receptacles 40 may be arranged such that plurality of first fasteners 401 and plurality of second fasteners 451 may be arranged in tray 22 in a plurality of groupings of eight or fewer fasteners. Each grouping corresponds to a particular one of a number of distinct fastener lengths. As shown in the present example, first receptacles 38 and second receptacles 40 are arranged in groupings, such that each grouping may contain up to eight fasteners (four of first fasteners 401 and four of second fastener 451) of the same shaft length. The number of receptacles within each groupings may vary in other embodiments. For example, each grouping may include two, four or six receptacles for containing fasteners.

When lid 12 is opened, the user may easily grasp the exposed end of each fastener and remove it from shelf 36. Alternately, the user may pick each fastener from shelf 36 using the drive instrument to be described. Since each single-use kit may include only the number of first fasteners 401 and second fasteners 451 required for the particular surgical indication, with a few extra, a number of first receptacles 38 and second receptacles 40 may be empty.

Also as shown in FIGS. 4 and 5, shelf 36 includes a plurality of fastener length gages 42, each of which is configured and labeled by a size label 44 for measuring incremental lengths of first fasteners 401 and second fasteners 451. The incremental lengths may range, for example, between 8 mm and 24 mm by 2 mm increments. Each of length gages 42 has a seat 62, a channel 64 and a stop 66. As shown in FIG. 5, when first fastener 401 of a particular, incremental length is mated into the appropriate one of gages 42, first fastener 401 fully fills that particular length gage without extending beyond seat 62. Using length gages 42, the surgeon may quickly confirm the length of a selected fastener prior to implantation of the fastener into the patient, thus ensuring that the fastener is of sufficient length to properly engage bone, but not so long as to protrude too far from the bone and into soft tissue.

Still referring to FIG. 4, DVR kit 100 includes container 10 and a plurality of components that include a first DVR assembly 102, a plurality of first fasteners 401, and a first drive instrument 70. The surgeon may use first driver instrument 70 to transmit a torque and drive each of first fasteners 401 into bone. The plurality of components of DVR kit 100 includes a depth gage 380 and at least one drill wire 370. Each of the single-use kit embodiments disclosed herein contains a vertically stacked, plurality of wire drills 370 that are retained between one of tray sides 24 and one of partitions 34 of tray 22, such that the tips of wire drills 370 are shielded from the other components and the user's hands.

As shown in FIG. 4, DVR kit 100 includes twenty-four of first fasteners 401, although the quantity may vary. An appropriate quantity of first fasteners 401 of various lengths may be based on historical data for similar, distal volar radius fracture procedures, with a few more fasteners provide to allow for special circumstances (dropped or damaged fasteners, unusual fractures, etc.).

First DVR assembly 102 includes a first DVR bone plate 104 preassembled with a plurality of first drill guides 330. The surgeon may use such preassembled drill guides to guide a wire drill when drilling holes into the fractured bone, so that the drilled holes are properly aligned with the apertures of the bone plate, and while also protecting the internal threads of the apertures. Such preassembled drill guides may also be useful for reshaping the bone plate using special bending instruments that fit over the drill guides. After drilling each hole, the surgeon may insert a drive end 80 of drive instrument 70 into drill guide 330 and remove drill guide 130 from plate 104.

Figure 6:
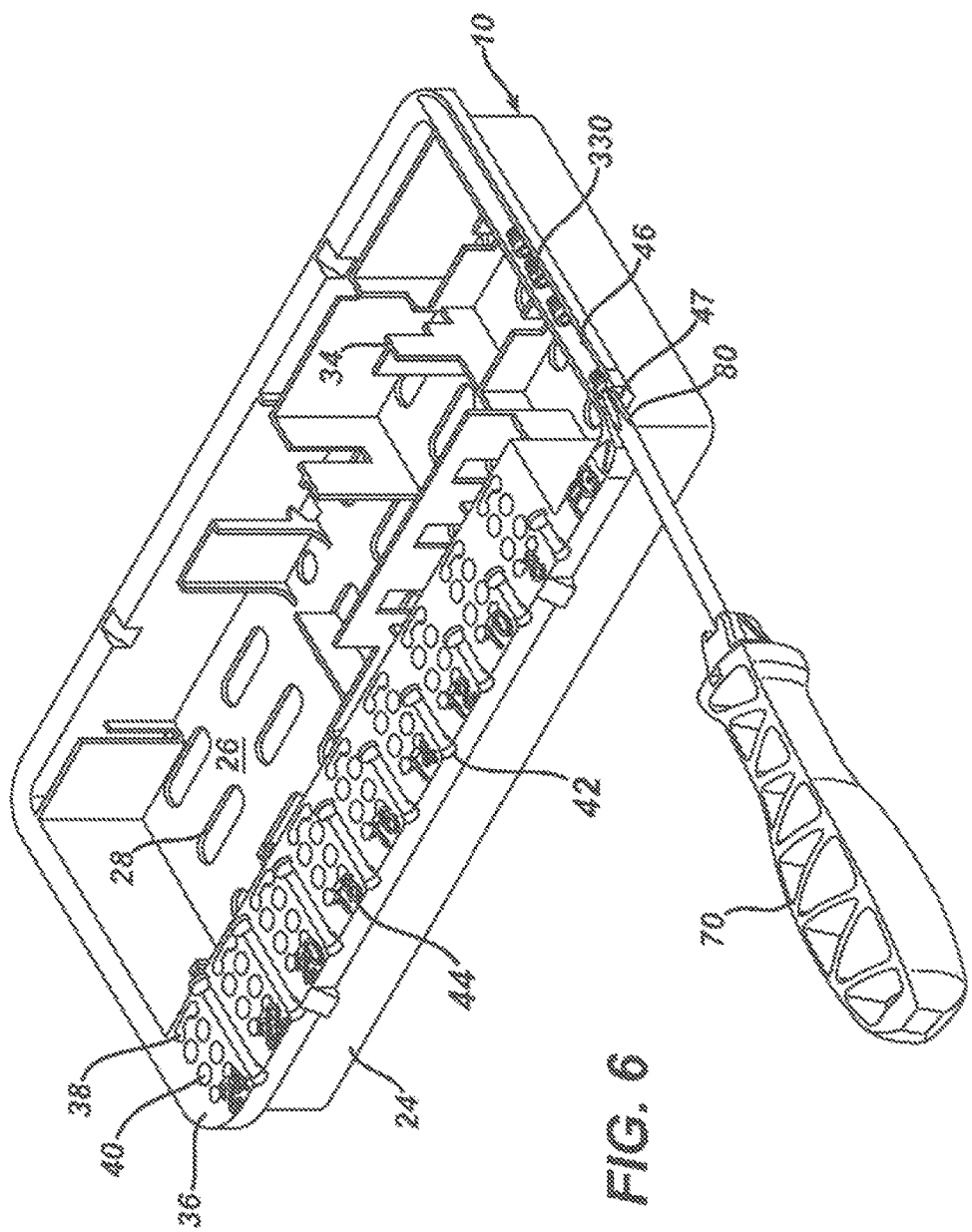
FIG. 6 is a top perspective, detailed view of another part of the DVR kit of FIG. 4, showing a drill guide as it is removed from a driver and placed into a reservoir of the container.

As shown in FIG. 6, each of a reservoir 46 and a stripping slot 47 is integrally formed into container 10. The surgeon may use stripping slot 47 to remove drill guide 330 from drive instrument 70, such that drill guide 330 falls into reservoir 46. In the embodiment shown, the user may collect a plurality of drill guides in a easily visible, linear arrangement, such that the user can quickly account for the number of drill guides 330 that have been removed from plate 104. An instructive label 48 (the letters "FG" stand for Fast Guide™) aids the "first-time" user in understanding where to discard drill guides 330.

Figure 7:
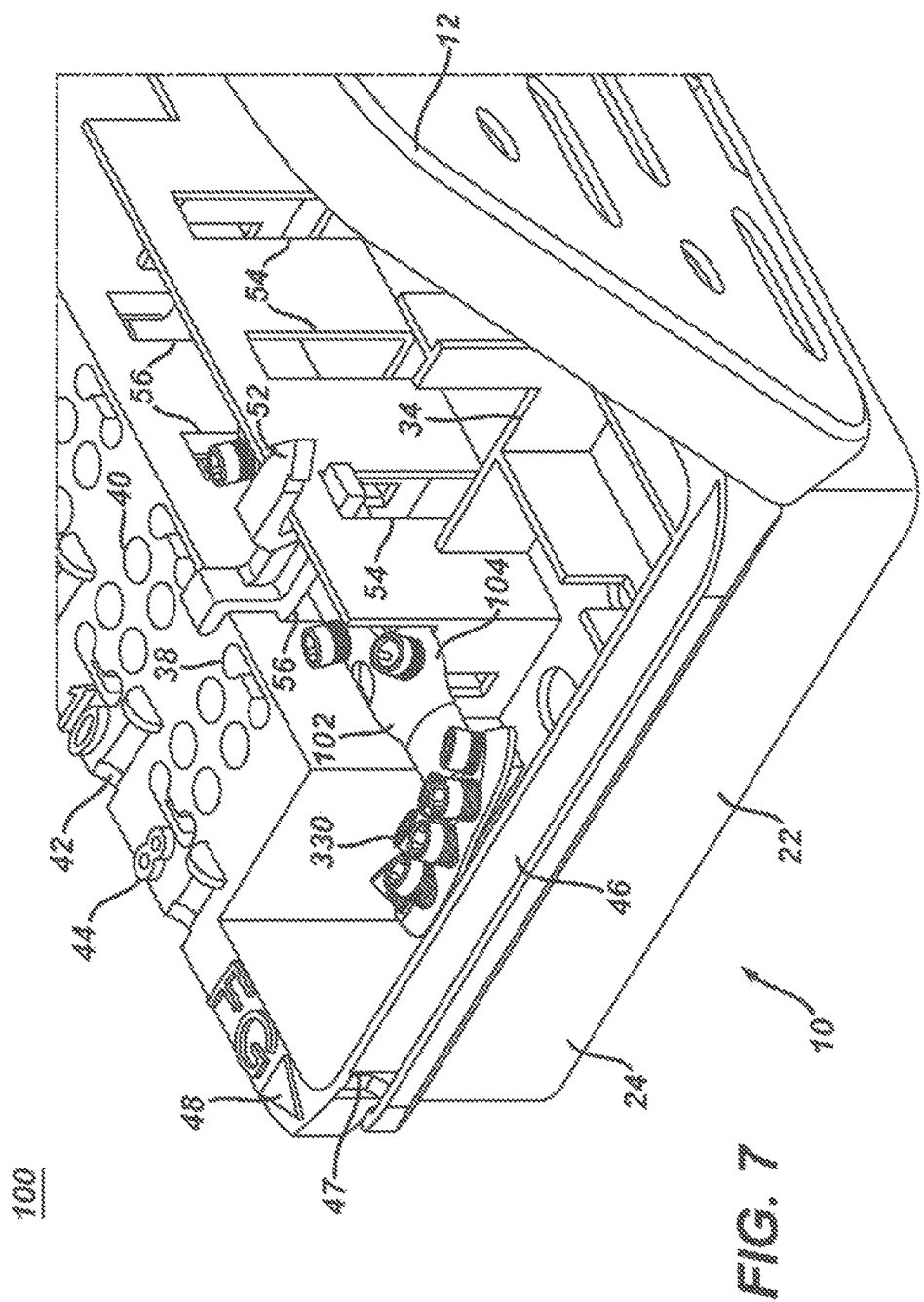
FIG. 7 is a top perspective, detailed view of another part of the DVR kit of FIG. 4, showing a retaining clip holding a DVR assembly in the container.

FIG. 7 is a top perspective, detailed view of part of DVR kit 100, showing a retaining clip 52 holding DVR assembly 100 between partitions 34 of container 10. First slots 54 and second slots 56 are formed into container 10, and clip 52 is configured, such that clip 52 may removably lock into one of first slots 54 and its opposing one of second slots 56. Clip 52 straddles over and retains DVR assembly 100, and is easily removable so that DVR assembly 100 may be lifted out of container 10. When container 10 is in the closed configuration, lid 12 abuts and holds clip 52 in place. In this embodiment of container 10, three pairs of slots 54 and 56 are provided to allow placement of clip 52 in three different positions. This allows container 10 to have the versatility to contain different types of bone plate assemblies FIG. 8 is a top perspective view of the single-use, DVR long 490 kit, which includes container 10 and a plurality of components, including a DVR long plate assembly 492, a plurality of first fasteners 401, a plurality of second fasteners 451, a plurality of wire drills 370, a second driver 90 and a depth gage 380. DVR long plate assembly 492 includes a plurality of first drill guides 330 preassembled to a DVR long plate 494. DVR long plate 494 includes a plurality of apertures of different types to be described, such that the user may attach DVR long plate 494 to the fractured bone using at least a portion of each of the plurality of first fasteners 401 and the plurality of second fasteners 451. (All bone plate apertures described herein should be understood to be fastener apertures, as opposed to K-wire apertures, suturing apertures, etc.)

FIG. 9 is a top perspective view of the single-use, fibula kit 200, which includes container 10 and a plurality of components, including a fibula plate assembly 202, plurality of first fasteners 401, plurality of second fasteners 451, plurality of wire drills 370, second driver 90 and depth gage 380. Fibula plate assembly 202 includes a plurality of second drill guides 340 preassembled to a fibula plate 204. Fibula plate 202 includes a plurality of apertures of different types to be described, such that the user may attach fibula plate 204 to the fractured bone using at least a portion of each of the plurality of first fasteners 401 and the plurality of second fasteners 451.

FIG. 10 is a top perspective view of the single-use, dorsal nail plate 210 (or DNP) kit, which includes container 10 and a plurality of components, including a DNP plate assembly 212, a plurality of first fasteners 401, a plurality of wire drills 370, first driver 70 and depth gage 380. Nail plate assembly 212 includes a DNP plate 494 removably attached to a DNP handle 216. DNP plate 494 includes a plurality of apertures to be described, such that the user may attach DNP plate 494 to the fractured bone using at least a portion of each of the plurality of first fasteners 401.

FIG. 11 is a top perspective view of the single-use, flexible fragment fixation (or F3) kit 220, which includes container 10 and a plurality of components, including a F3 plate assembly 222, plurality of first fasteners 401, plurality of wire drills 370, first driver 70 and depth gage 380. F3 plate assembly 222 includes a F3 plate 224 having a plurality of apertures to be described, such that the user may attach F3 plate 224 to the fractured bone using at least a portion of each of the plurality of first fasteners 401. F3 kit 220 is particularly suitable for the internal fixation of a fractured, distal ulna bone, and therefore may also be referred to as a distal ulna kit.

FIG. 12 is a top perspective view of the single-use, proximal radius kit 240, which includes container 10 and a plurality of components, including a proximal radius plate assembly 242, a plurality of first fasteners 401, a plurality of wire drills 370, first driver 70 and depth gage 380. Proximal radius plate assembly 242 includes a proximal radius plate 244 having a plurality of apertures to be described, such that the user may attach proximal radius plate 244 to the fractured bone using at least a portion of each of the plurality of first fasteners 401.

FIG. 13 is a top perspective view of the navicular kit 230, which includes container 10 and a plurality of components, including a navicular plate assembly 230, a plurality of second fasteners 451, a plurality of wire drills 370, second driver 90 and depth gage 380. Navicular plate assembly 230 includes a plurality of second drill guides 340 preassembled with a navicular plate 236 having a plurality of apertures to be described, such that the user may attach navicular plate 244 to the fractured bone using at least a portion of each of the plurality of first fasteners 401. Navicular plate assembly 232 is removably retained upon a board insert 234 that, in turn, is retained within container 10 by a pair of T-rails 68 integrally formed into container 10.

Figure 14:
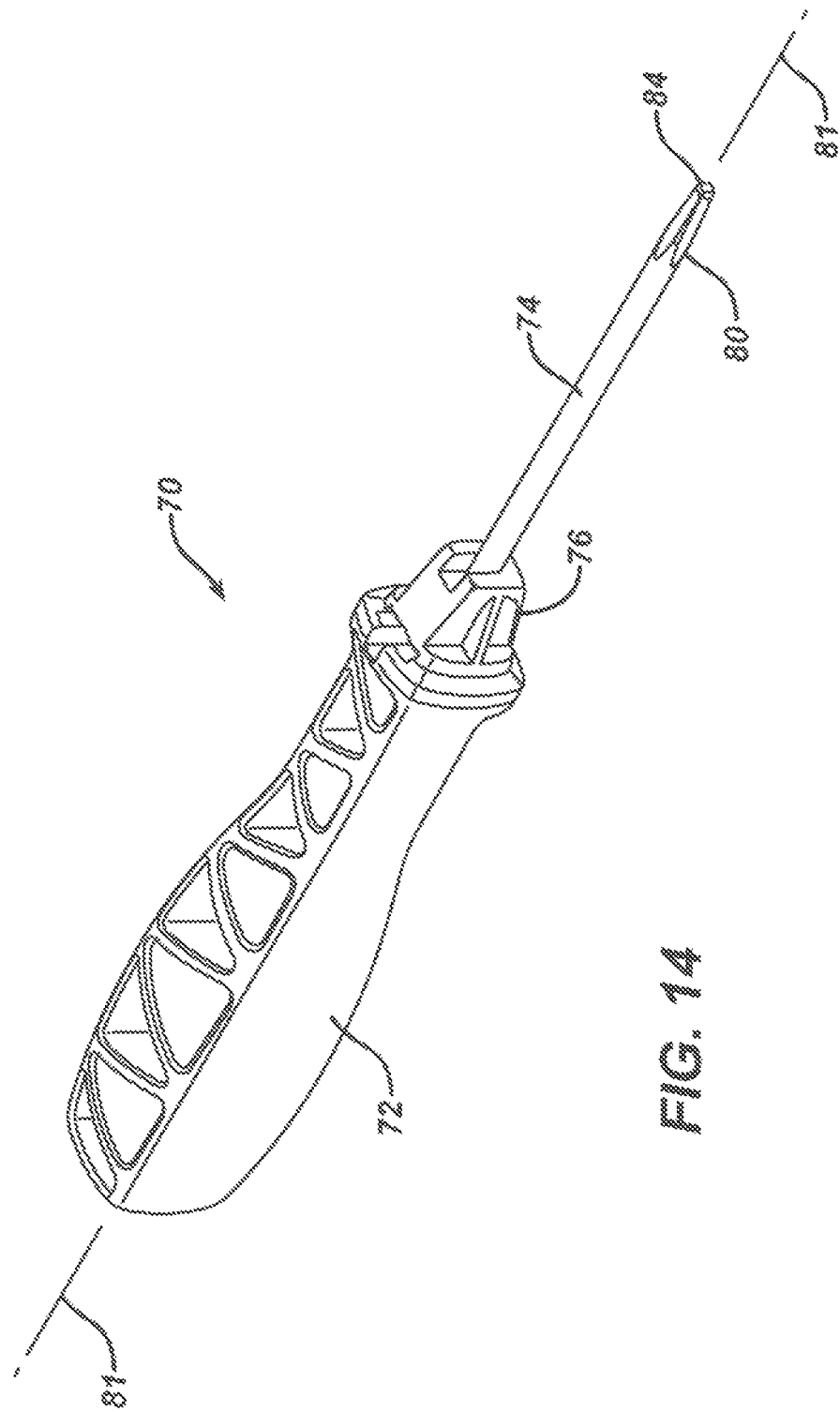
FIG. 14 is a perspective view of a first drive instrument, which has a first drive tip.

FIG. 14 is a perspective view of first drive instrument 70, which has a handle 72 connected by an attachment 76 to a shaft 74 that defines a longitudinal axis 81. At the distal end of shaft 74 is a first drive end 80 that includes a first drive tip 84. Handle 72 may be formed from a rigid, high strength polymer. Shaft 74 may be formed from a stainless steel and has a proximal end (not visible in the figures) that is configured to be retainably insert-molded into handle 72 at attachment 76. As will be further described in conjunction with FIG. 25, first drive tip 84 is configured for use with first fastener 401.

Figure 15:
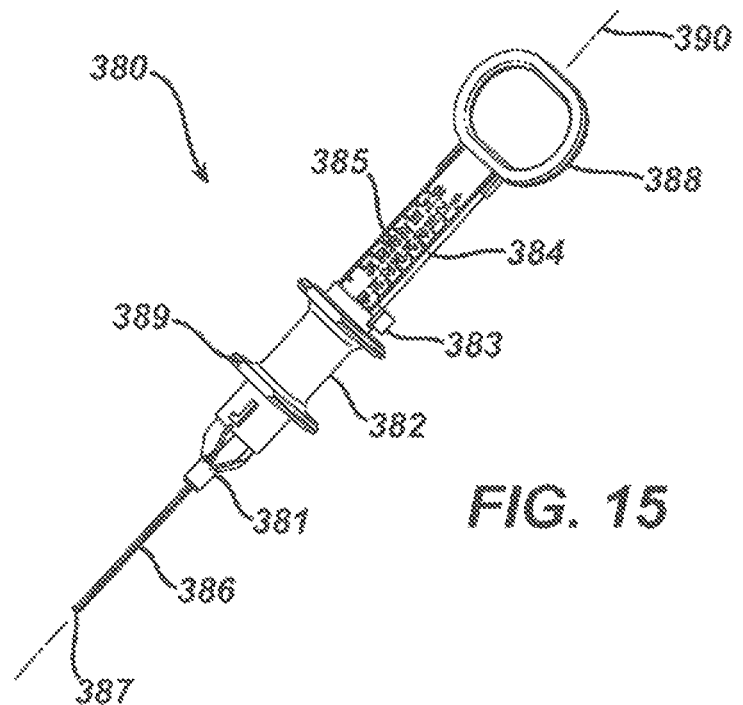
FIG. 15 is a perspective view of a depth gage for measuring the length of a hole extending through an aperture of a bone plate and a coaxially drilled hole in the bone, the depth gage shown in an extended position.
Figure 16:
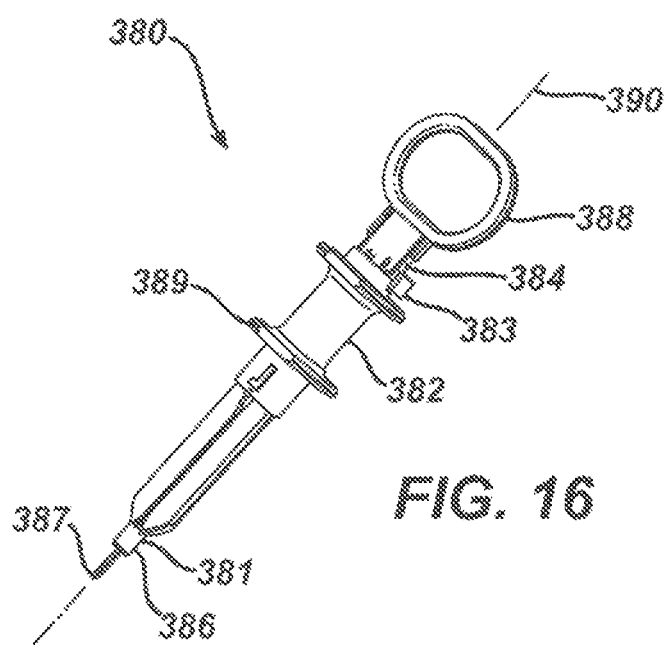
FIG. 16 is a perspective view of the depth gage of FIG. 15, shown in a retracted position.

FIG. 15 is a perspective view of depth gage 380 for measuring the length of a hole extending through an aperture of a bone plate and a coaxially drilled hole in the bone, shown in an extended position. FIG. 16 is a perspective view of depth gage 380, shown in a retracted position. Depth gage 380 includes a body component 382 that frictionally fits over a slide component 384 having a distal and proximal end defining a longitudinal axis 390 therebetween. Body component 382 is adjustably movable along slide component 384 along longitudinal axis 390. Each of body component 382 and slide component 384 may be injection molded from a rigid polymer. A feeler wire 386, which may be formed from stainless steel, is attached to body component 382 and extends distally along longitudinal axis 390 from the distal end of slide component 384. Feeler wire 386 includes a hook tip 387. A ring 388 is connected to the proximal end of slide component 384 and is sized and shaped for a thumb of the user. A spool portion 389 of body component 382 is sized and shaped for placement between, for example, the fore and middle fingers of the user. The slide component 384 includes indicia 385 that corresponds to the length of feeler wire 386 extending distally from the distal end of slide component 384. The position of body component 382 is adjustable between a first stop 381 and a second stop 383 on slide component 384. The frictional fit between slide component 384 and body component 382 is sufficient to maintain this position when the user releases depth gage 380.

The user may measure the length of the aperture through the plate and bone, and thereby determine the length of the fastener needed, by first fully extending feeler wire 386, then catching hook tip 387 on the edge of the aperture on the far side of the bone. Then the user adjusts spool portion 389 and ring 388 towards each other until the distal end of slide component 384 abuts the top surface of the bone plate. The user may read the indicia 385 that aligns with the proximal end of body component 382 and corresponds to the length of the aperture. Depth gage 42 may also be used through a drill guide preassembled to the plate, in which case, the user may read the indicia 385 that aligns with the proximal end of second stop 383.

Figure 17:
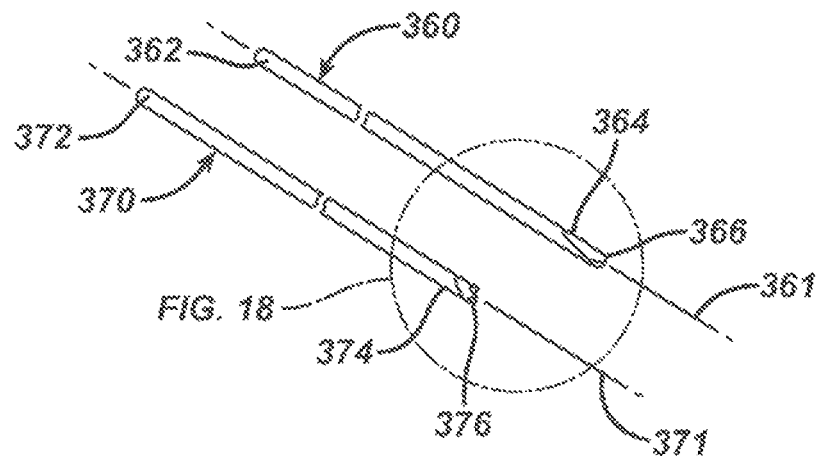
FIG. 17 is a perspective view of a pair of wire drills.
Figure 18:
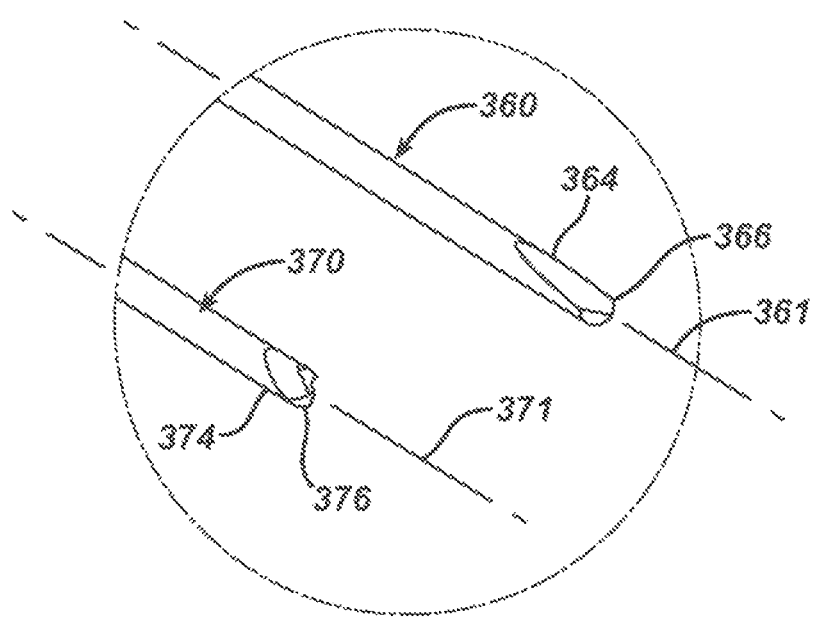
FIG. 18 is a perspective, detail view of the distal ends of the wire drills shown in FIG. 17.
Figures 19, 20, 21:
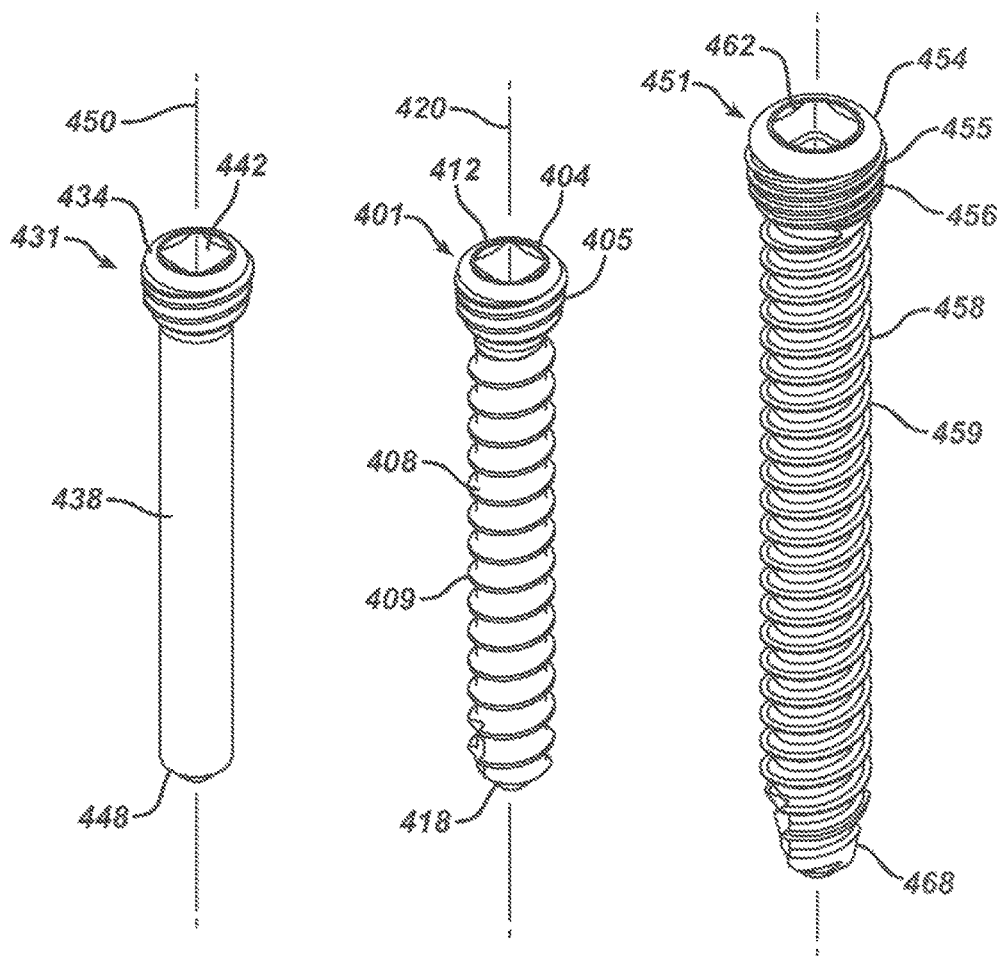
FIG. 19 is a perspective view of a first fastener, according to a second embodiment.
FIG. 20 is a perspective view of a first fastener, according to a first embodiment.
FIG. 21 is a perspective view of a second fastener.

FIG. 17 is a perspective view of wire drill 370 and an alternate wire drill 360. FIG. 18 is a perspective, detail view of the distal ends of wire drill 370 and alternate wire drill 360. Each of wire drill 370 and alternate wire drill 360 may be formed from a stainless steel and are well known in the art for drilling holes in bone, for the provisional fixation of fractured bones, for provisional attachment of bone plates to bone, and for other uses. Wire drill 370 has a proximal end 372, a distal end 373, a longitudinal axis 371 extending therebetween, and a fluted tip 376. Wire drill 360 has a proximal end 362, a distal end 364, a longitudinal axis 361 extending therebetween, and a spade tip 366. Each of the single-use kits disclosed herein may contain at least one of alternate wire drill 360 and/or at least one of wire drill 370. In general, wire drill 370 may be used to prepare a pilot hole in bone for one of first fastener 401 and second fastener 451, so the diameter of wire drill 370 is appropriately sized accordingly. One version of wire drill 360 may be what is known in the art as a K-wire, which is primarily used for provisional fixation, and may be provided, for example, with a diameter of about 1.6 mm. The surgeon may insert the K-wire through any one of the aforementioned apertures of the bone plates described herein, but it is well-known in the art that these plates may also include one or more smaller holes specifically for receiving K-wires and/or for attaching sutures thereto FIGS. 19, 20 and 21 are perspective views of the same scale showing the fasteners that may be included in the single-use kits described herein. FIG. 20 is a perspective view of first fastener 401. FIG. 19 is a perspective view of an alternate embodiment of first fastener 401, also referred to as a first fastener peg 431. FIG. 21 is a perspective view of second fastener 451. Each of first fastener 401, first fastener peg 431 and second fastener 451 may be formed from a metal such as a titanium alloy such as $Ti_6Al_4V$ that is anodized for anti-galling and abrasion resistance. First fastener 401 and first fastener peg 431 may have a nominal size of 2.7 mm and second fastener 451 may have a nominal size of 3.5 mm.

First fastener 401 has a head 404 and a shaft 408 that defines a longitudinal axis 420. Shaft 408 may be provided in a number of incremental lengths, ranging from 8 mm to 24 mm by increments of 2 mm, for example. Head 404 includes a plurality of external threads 405 and a drive socket 412 that has an approximately square configuration. Shaft 408 has a plurality of threads 409 and a tip 418 and is configured for self-tapping into a properly sized, drilled hole in the bone.

Figure 22:
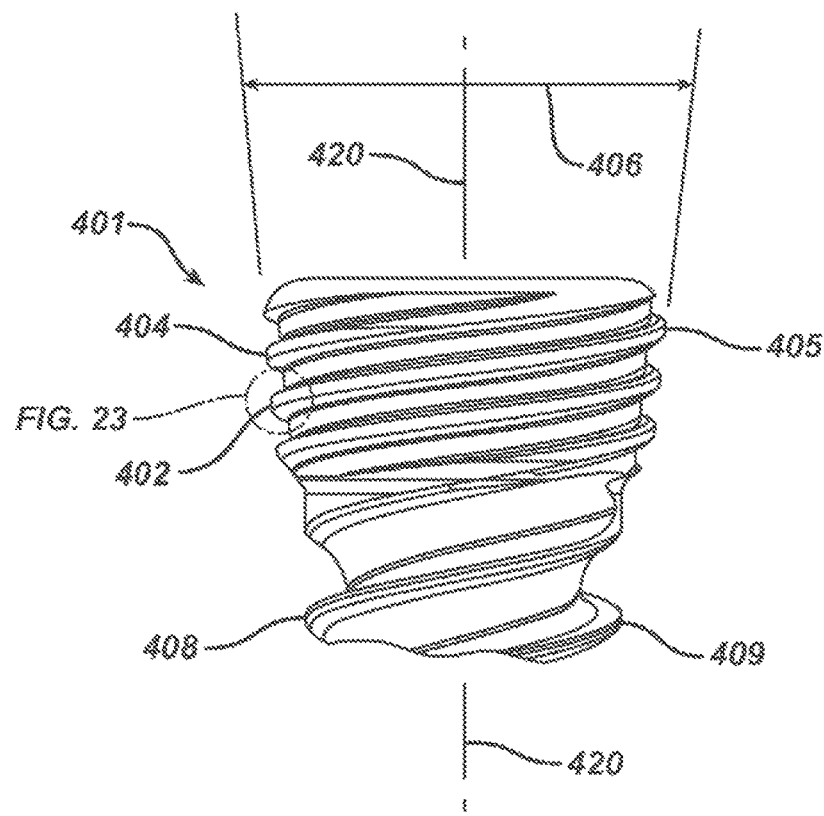
FIG. 22 is a detail view of a first tapered, threaded head of the first fastener shown in FIG. 20.
Figure 23:
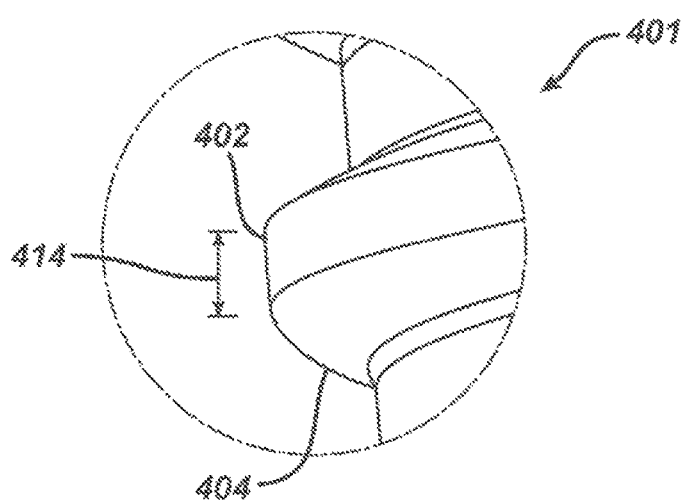
FIG. 23 is a detail view of a crest portion of a thread of the first tapered, threaded head of FIG. 22.

FIG. 22 is a detail view of head 404 of first fastener 401 shown in FIG. 20. Threads 405 are conically tapered and define a taper angle 406 of about 12 degrees, centered on longitudinal axis 420. Threads 405 may have a double-lead type of thread as shown in FIG. 22. Head 404 is adapted for locking at a fixed angle into a tapered, threaded (locking) aperture of a bone plate, as is known in the art. But as will be described herein, head 404 is also adapted for use in particular non-threaded (non-locking) apertures. This is primarily due to the inclusion on threads 405 of crest portions 402 that have a crest width 414 (FIG. 23

Crest width 414, as shown in FIG. 22, is 0.141 millimeters, but may be approximately in the range of 0.120 to 0.160 millimeters. A pitch distance between adjacent crest portions 402, as shown in FIG. 22, is 0.559, but may be approximately in the range of 0.500 to 0.600 millimeters. Therefore, a ratio of crest width 414 to pitch distance, as shown in FIG. 22, is 0.252, but may be approximately in the range of 0.200 to 0.320. Since crest portions 414 are relatively wide as compared to tapered, threaded heads of some currently available bone fasteners, first fastener 401 may be driven with high compressive force into a smooth (non-threaded) aperture in various trajectories, such that threads 405 are not "rolled over" or otherwise damaged during insertion. Without widened, crest portion 414 on threads 405, it may be more likely that head 404 would "pull through" the aperture of the plate under high compressive load.

First fastener peg 431, shown in FIG. 19, includes a head 434 having a drive socket 442 and may be identical to head 404 of first fastener 401. First fastener peg 431 also includes a smooth shaft 438, a rounded tip 448 and a longitudinal axis 450. Like shaft 408 of first fastener 401, shaft 438 may be provided in a number of incremental lengths, ranging from 8 mm to 24 mm by increments of 2 mm, for example. First fastener peg 431 is primarily used in locking (threaded) apertures.

As shown in FIG. 21, second fastener 451 includes a head 454, a shaft 458 and a longitudinal axis 470. Head 454 includes tapered threads 455 that may be a triple-lead type thread and include crest portions 456 that provide the same advantages as described for threads 405 of first fastener 401. As shown in FIG. 21, tapered threads 455 may have similar dimensions for crest width and pitch distance, as compared to first fastener 401 of FIG. 22. Shaft 458 has threads 459 and a tip 468 that may be conventionally designed for self-tapping into a drilled hole in the bone. Second fastener 451 may also be provided, for example, in the single-use kits described herein with lengths in the range of approximately 8 mm to 24 mm in 2 mm increments.

Figure 24:
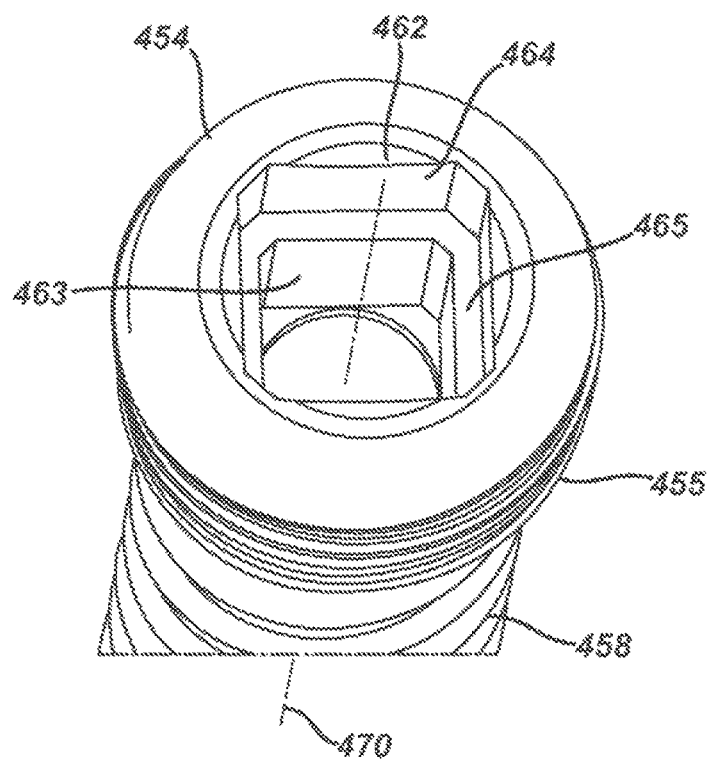
FIG. 24 is a perspective, detail view of a double socket of the second fastener shown in FIG. 21.

FIG. 24 is a perspective, detail view of head 454 and a portion of shaft 458 of second fastener 451 shown in FIG. 21. Head 454 includes a double-socket 462 that is sized and shaped for optimal use with second drive instrument 90 (to be described next for FIG. 26), although it may also be used with first drive instrument 70. Double-socket 462 includes a distal recess 463 that is adjacent and coaxial to a proximal recess 464 on longitudinal axis 470. Each of proximal recess 464 and distal recess 463 may have an approximately square configuration with each pair of opposing sides on proximal recess 464 parallel to a corresponding pair of opposing sides on distal recess 463. The height of distal recess 463 may be greater than the height of proximal recess 464. Proximal recess 464 is wider than distal recess 463, thereby forming a ledge 465 and fitting easily within the tapered shape of head 454 without weakening threads 455.

Figure 26:
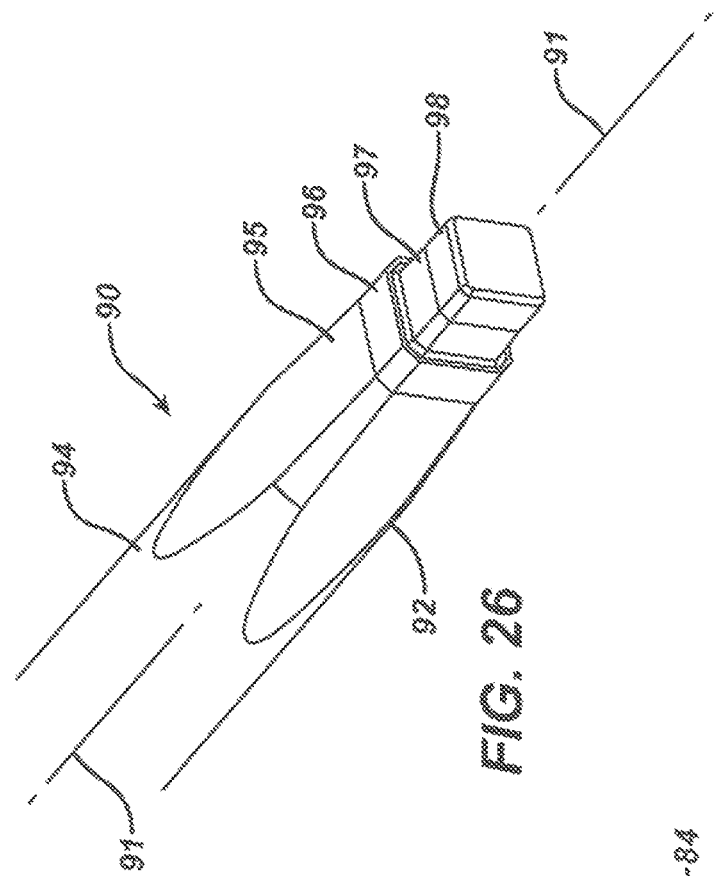
FIG. 26 is a perspective, detail view of a second drive tip.
Figure 25:
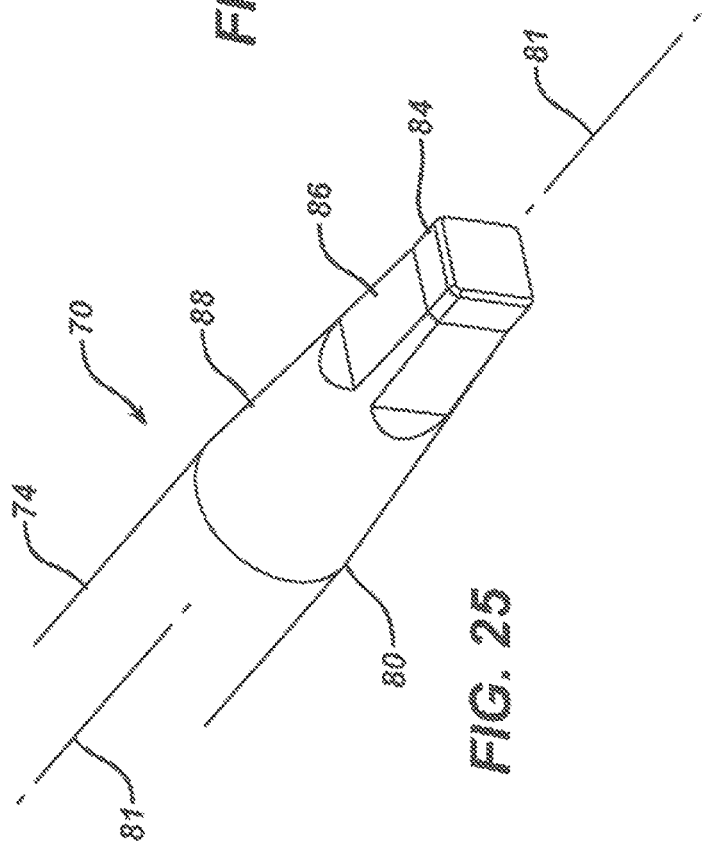
FIG. 25 is a perspective, detail view of the first drive tip shown in FIG. 14.

FIG. 25 is a perspective view of first drive end 80 of first drive instrument 70. FIG. 26 is a perspective view of second drive end 92 of second drive instrument 90. Each of first drive instrument 70 and second drive instrument 90, also referred to as torque drivers, may be use to drive each of first fastener 401 (including first fastener peg 431) and the larger, second fastener 451. However, second drive instrument 90 may be used to transmit more torque to second fastener 451 than what is possible using first drive instrument 70.

As shown in FIG. 25, drive end 80 includes a conical portion 88 that transitions distally, in the direction of axis 81, shaft 74 to a square taper portion 86, which in turn transitions to a square drive tip 84. When drive tip 84 is fully inserted into either one of drive socket 412 of first fastener 401 or double-socket 462 of second fastener 451, a portion of square taper 86 wedges into the non-tapered sidewalls of either drive socket 412 or double-socket 462, respectively. This feature causes either one of first fastener 401 or second fastener 451 to "stick" to the drive end of either one of first drive instrument 70 or second drive instrument 451, to facilitate removal of each fastener from container 10 and to position the fastener into one of the apertures of the bone plate and partially into the drilled hole in the bone prior to transmitting torque to drive the fastener into the bone.

As shown in FIG. 26, drive end 92 includes a first tapered square portion 95 that transitions distally, in the direction of axis 91, shaft 94 to a first square drive portion 96. A second tapered portion 97 extends distally along axis 91 to a second square drive portion 98 that is smaller than first square drive portion 96. When drive tip 92 is fully inserted into either one of drive socket 412 of first fastener 401 or double-socket 462 of second fastener 451, a portion of second square taper portion 97 wedges into the non-tapered sidewalls of either of drive socket 412 or double-socket 462, respectively. When drive end 92 is fully inserted into double-socket 462 of second fastener 451, at least one of first tapered portion 95 or second tapered portion 97 stick into double-socket 462. This also serves to aid the surgeon in the pick-up and placement of the fasteners. For obvious reasons, when a limited number of fasteners are readily available, it is highly desirable to avoid dropping fasteners into the wound site of the patient or onto a non-sterile surface in the operating room.

Figure 27:
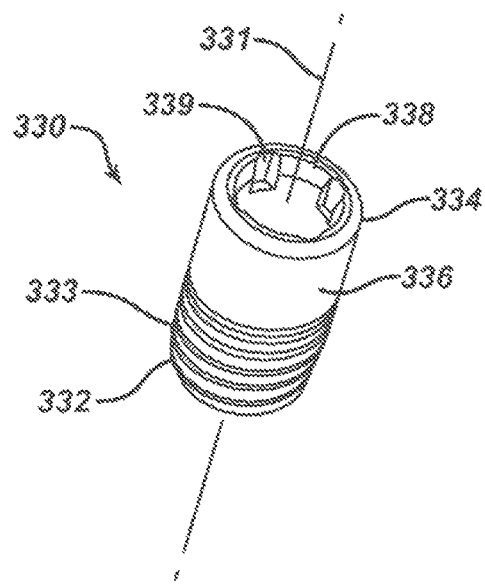
FIG. 27 is a perspective view of a first drill guide.

FIG. 27 is a perspective view of a first drill guide 330 for use with one of the appropriately sized, wire drills 370, to drill a hole into bone for receiving first fastener 401. A plurality of first drill guides 330 may be preassembled with bone plates as previously shown in FIGS. 4, 8, 11 and 12. First drill guide 330 includes a body 336 having a distal end 332, a proximal end 334, and a bore 338 sized and shaped to guide the appropriately sized wire drill 370 and defining a longitudinal axis 331. Distal end 332 includes threads 333 for removable attachment to a threaded aperture of a bone plate. Proximal end 334 includes four indentations 339 spaced evenly apart on the periphery of bore 338 for receiving square drive tip 84 of first drive instrument 70 and second drive portion 98 of second drive instrument 90.

Figure 28:
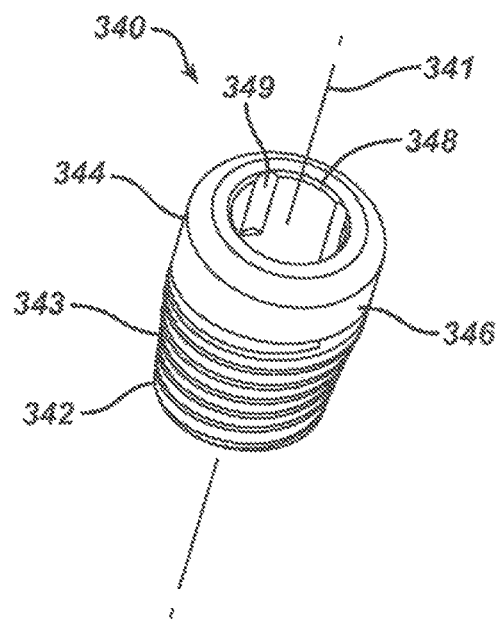
FIG. 28 is a perspective view of a second drill guide.

FIG. 28 is a perspective view of a second drill guide 340 for use with one of the appropriately sized, wire drills 370, to drill a hole into bone for receiving second fastener 451. A plurality of second drill guides 340 may be preassembled with bone plates as previously shown in FIGS. 9 and 13. Second drill guide 340 includes a body 346 having a distal end 342, a proximal end 344, and a bore 348 sized and shaped to guide the appropriately sized wire drill 370 and defining a longitudinal axis 341. Distal end 342 includes threads 343 for removable attachment to a threaded aperture of a bone plate. Proximal end 344 includes four indentations 349 spaced evenly apart on the periphery of bore 348 for receiving square drive tip 84 of first drive instrument 70 and second drive portion 98 of second drive instrument 90.

Figure 29:
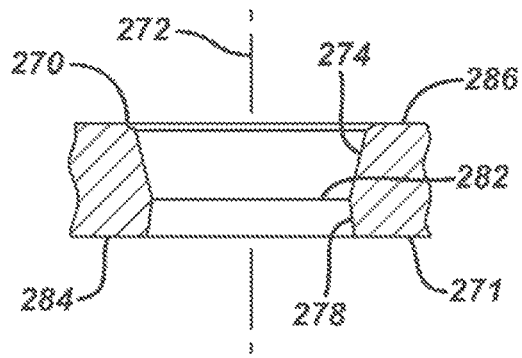
FIG. 29 is a cross-sectional view of a non-locking aperture.
Figure 30:
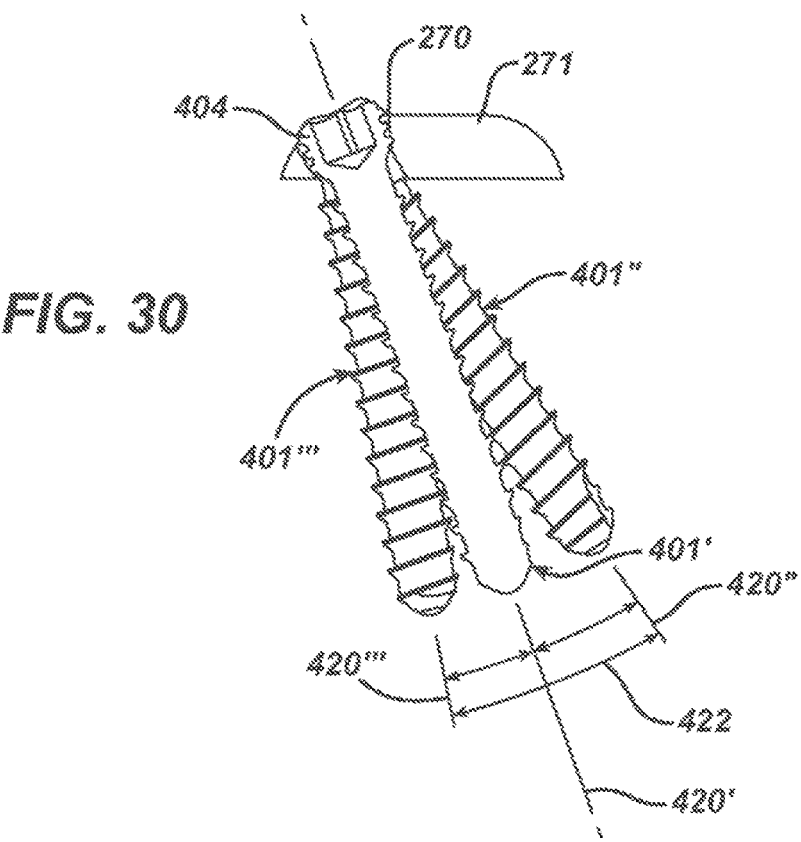
FIG. 30 is a cross-sectional view of a bone plate showing three possible trajectories of the first fastener of FIG. 20 inserted into the non-locking aperture of FIG. 29.

FIG. 29 is a cross-sectional view of a non-locking aperture 270 that may be sized to receive first fastener 401. (The term "aperture", as used herein, is interchangeable with the term "hole".) Similarly, although not shown in detail views in the figures, non-locking aperture 270 may also be sized to receive second fastener 451. FIG. 30 is a cross-sectional view of a portion of a bone plate 271 (for no particular surgical indication, but shown for description purposes), showing three possible trajectories of first fastener 401 of FIG. 20 inserted into non-locking aperture 270 of FIG. 29. Non-locking aperture 270 extends between a top surface 286 and a bottom surface 284 of a plate 271 and defines an axis 272. Non-locking aperture 270 has a conical upper portion 274 and tapers from top surface 286 towards the middle of plate 271. A conical lower portion 278 is coaxial with conical upper portion 274 and tapers from bottom surface 284 towards the middle of plate 271 to form a waist 282 with conical upper portion 274. The position and orientation of waist 282 relative to top surface 286 may vary, but as shown in FIG. 29, is deep enough to receive head 404 of first fastener 401, such that head 404 is not proud to top surface 286. As shown in FIG. 30, first fastener 401 may be inserted through plate 271 in any desired trajectory within a range defined by a conical angle 422, wherein axes 401', 401" and 401'" define three possible trajectories of first fastener 401 within that range. This multidirectional ability allows the surgeon to form a polyaxial non-locking compressive construct.

Figure 31:
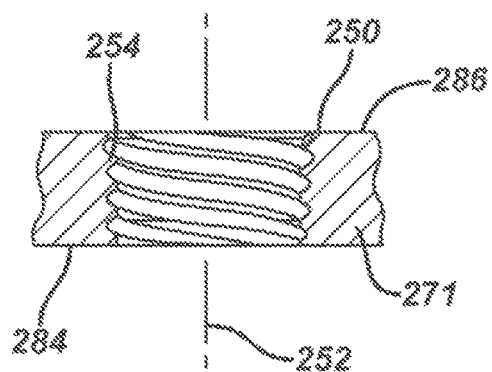
FIG. 31 is a cross-sectional view of a locking aperture.
Figure 32:
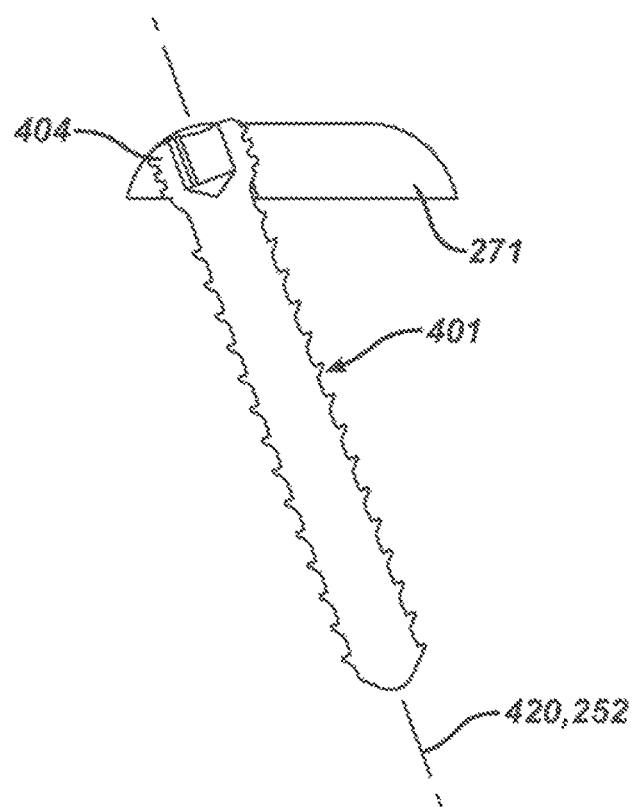
FIG. 32 is a cross-sectional view of a bone plate with the first fastener of FIG. 20 inserted at a fixed angle into the locking aperture of FIG. 31.

FIG. 31 is a cross-sectional view of a locking aperture 250, which is very similar to other locking apertures of bone plates that are well-known in the art. FIG. 32 is a cross-sectional view of bone plate 271 with first fastener 401 of FIG. 20 inserted at a fixed angle into locking aperture 250. Similarly, although not shown in detailed views in the figures, locking aperture 250 may be sized to receive second fastener 451. Locking aperture 250 includes a tapered, threaded bore 254 for receiving head 404 of first fastener 401. Bore 254 extends between top surface 286 and bottom surface 284 of plate 271 and defines an axis 252. As shown in FIG. 32, when first fastener 401 is fully inserted into plate 271, axis 420 of first fastener 401 is coaxial with axis 252 of locking aperture 250. This arrangement allows the surgeon to form a fixed-angle locking construct.

FIG. 33 is a top view of a unidirectionally ramped (or UR) aperture 290. FIG. 34 is a cross-sectional view of UR aperture 290. FIG. 35 is a cross-sectional view of UR aperture 290 with first fastener 401 partially inserted therein. FIG. 36 is a cross-sectional view of UR aperture 290 with first fastener 401 fully inserted therein. UR aperture 290 may also be sized, although not shown in detail views in the figures, to receive second fastener 451. UR aperture 290 is a non-locking type of aperture for compressively attaching the bone plate against the bone. The surgeon may also use UR aperture 290 to aid in reduction of the bone fragments, i.e., the compression of bone fragments along the longitudinal axis of the bone plate, often referred to in the art as dynamic compression. As shown in FIGS. 35 and 36, proper insertion of first fastener 401 into UR aperture 290 causes plate 271 to shift in a direction depending on the orientation of UR aperture 290. As shown in FIGS. 33 and 34, UR aperture 290 has an upper conical portion 294 intersecting with a coaxially opposing, lower conical portion 298 to form a waist 282 about an axis 292, in an arrangement similar to non-locking aperture 270 of FIG. 29. UR aperture 290 further includes a circular bore portion 306 defining an axis 307 that is parallel and offset from axis 308. Circular bore portion 306 is sized to receive shaft 408 of first fastener 401, but is too small to receive head 404. The surgeon may drill a hole into bone that is approximately coaxial with axis 307 and then insert first fastener 401 as shown in FIGS. 35 and 36, such that head 404 tends to seat into upper conical portion 294, and "ramp" in a translation direction along plate axis 272. The translation distance possible is determined by an offset distance 308 between axis 292 and 307.

Figure 37:
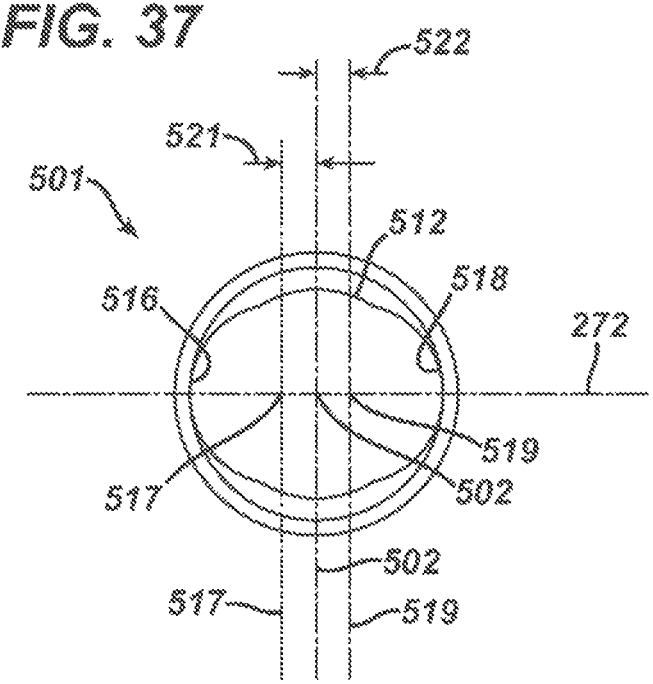
FIG. 37 is a top view of a bidirectionally ramped non-locking aperture.
Figure 38:
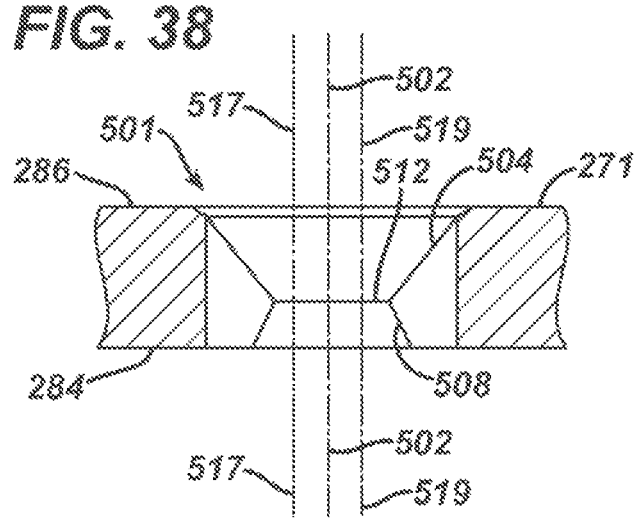
FIG. 38 is a cross-sectional view of the bidirectionally ramped non-locking aperture of FIG. 37.

FIG. 37 is a top view and FIG. 38 is a cross-sectional view of a bidirectionally ramped (BR) aperture 501, which is similar to UR aperture 290 of FIG. 34. BR aperture 501 may be sized to receive first fastener 401 or second fastener 451. The surgeon may use BR aperture 501 to compressively attach bone plate 271 against the bone, and also to dynamically compress the bone fragments along the longitudinal axis of plate 271 in either of opposing directions. This bidirectional feature allows the surgeon to reduce fragments on either side of BR aperture 501. BR aperture 501 includes an upper conical portion 504 defining an axis 502, a coaxial, lower conical portion 508, a waist 512, a first circular bore portion 516 defining an axis 517, and an opposing second circular bore portion 518 defining an axis 519. The surgeon may use BR aperture 501 with first fastener 401 to translate plate 271 an offset distance 521 in a first direction along axis 272 of plate 271, or an offset distance 522 in a second, opposing direction along axis 272.

Figure 39:
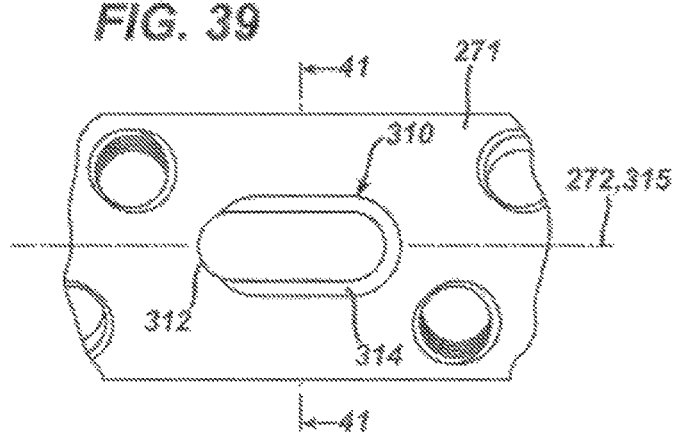
FIG. 39 is a top view of a unidirectionally ramped slot positioned along a longitudinal axis of a plate.
Figure 40:
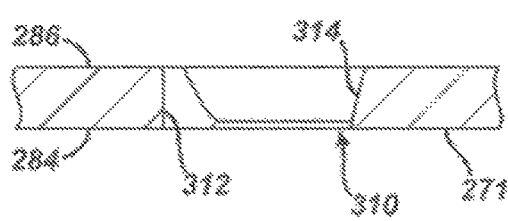
FIG. 40 is a cross-sectional view taken through the longitudinal axis of the plate of FIG. 39, showing a unidirectionally ramped slot.
Figure 41:
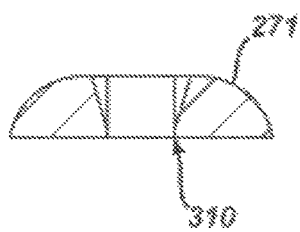
FIG. 41 is a cross-sectional view taken through line 41-41 of FIG. 39, showing the unidirectionally ramped slot of FIG. 39.
Figure 44:
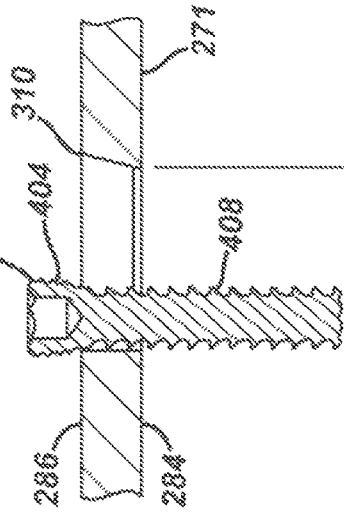
FIG. 44 is a cross-sectional view, taken through the longitudinal axis, of the first fastener partially inserted into the unidirectionally ramped slot as shown in FIG. 42.
Figure 45:
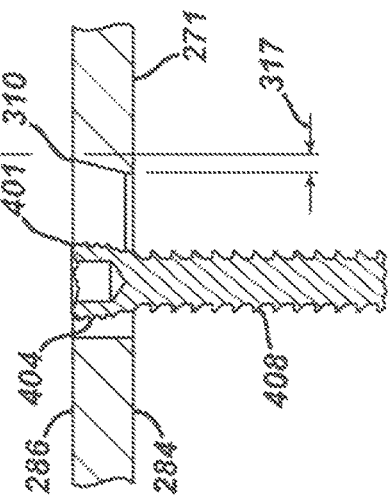
FIG. 45 is a cross-sectional view, taken through the longitudinal axis, of the first fastener fully inserted into the unidirectionally ramped slot as shown in FIG. 43.
Figure 42:
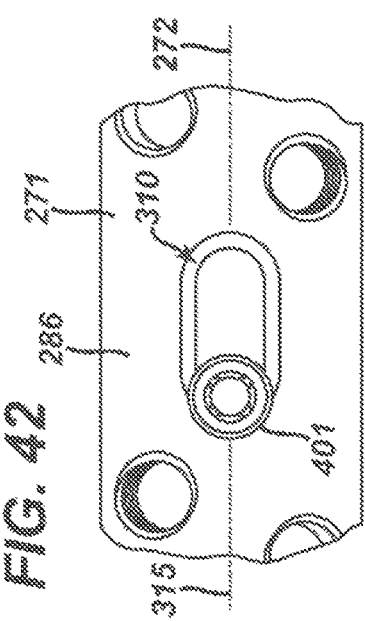
FIG. 42 is a top view of the first fastener partially inserted into the unidirectionally ramped slot of the bone plate.
Figure 43:
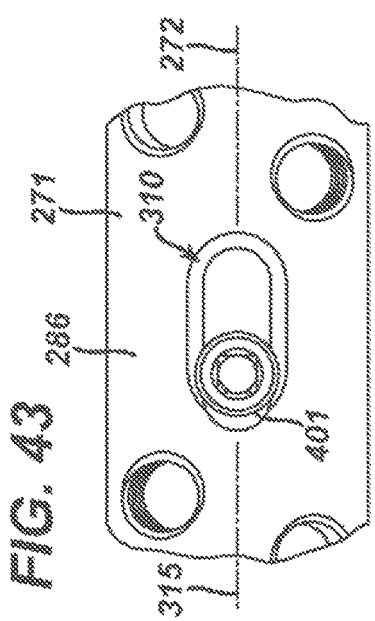
FIG. 43 is a top view of the first fastener fully inserted into the unidirectionally ramped slot.

FIG. 39 is a top view of a unidirectionally ramped (UR) slot 310 positioned along axis 272 of plate 271. FIG. 40 is a cross-sectional view of UR slot 310, taken through axis 272; FIG. 41 is a cross-sectional view of UR slot 310, taken through line 41-41 of FIG. 39; FIG. 42 is a top view of first fastener 401 partially inserted into UR slot 310; FIG. 43 is a top view of first fastener 401 fully inserted into the UR slot 310; FIG. 44 is a cross-sectional view, taken through axis 272, of first fastener 401 partially inserted into UR slot 310; FIG. 45 is a cross-sectional view, taken through axis 272, of first fastener 401 fully inserted into the UR slot 310. UR slot 310 is more elongated than UR aperture 290, and also may be used to dynamically compress bone fragments as first fastener 401 is inserted into bone. The use of slotted apertures similar to UR slot 310 in bone plates is well-known in the art for reducing bone fragments as the surgeon attaches the plate to the bone. UR slot 310 has an elongated, tapered portion 314 that defines a slot axis 315 and tapers from top surface 286 to bottom surface 284 of plate 271. A circular bore portion 312 is formed into one end of tapered portion 314 and is sized to receive shaft 408 of first fastener 401, but not head 404. As the surgeon inserts first fastener 401 into bone as shown in FIGS. 44 and 45, head 404 tends to seat into tapered portion 310 and move plate 271 in a direction along axis 272 a distance 317 (FIG. 45).

Figure 46:
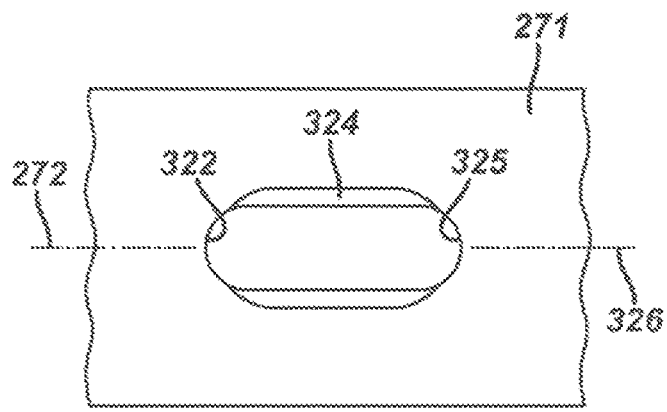
FIG. 46 is a top view of a bidirectionally ramped slot in a bone plate.
Figure 47:
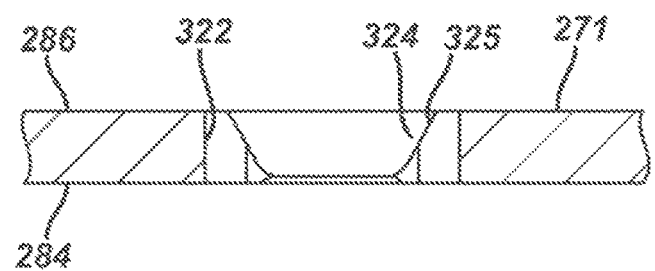
FIG. 47 is a cross-sectional view, taken through the longitudinal axis, of the bidirectionally ramped slot of FIG. 46.

FIGS. 46 and 47 shown a bidirectionally ramped (BR) slot 320 that is similar to UR slot 310, except the surgeon may use BR slot 320 to dynamically compress bone fragments in either of opposing directions along axis 292 of plate 271. BR slot 320 includes an elongated, tapered portion 325 that tapers from top surface 286 to bottom surface 284 of plate 271. A first circular bore portion 322 and a second circular bore portion 325 are formed into opposing ends of tapered portion 325.

Each of UR slot 310 and BR slot 320 may be sized to receive either first fastener 401 or second fastener 451.

FIG. 48 is an end view, FIG. 49 is a top view, and FIG. 50 is a perspective view of a first DVR assembly 102 that was earlier described for FIG. 4. First DVR assembly 102 includes a first DVR plate 104 that has a head 106, a neck 108 and a shaft 110 that extends along a longitudinal axis 111.

Head 106 includes a plurality of locking apertures 250, each of which is assembled with a first drill guide 330. Each of locking apertures 250 of head 106 defines a desired, fixed trajectory, such that insertion of first fastener 401 into each locking aperture 250 of head 106 provides subchondral support of the articulation surface of the wrist joint of the distal radius.

Shaft 110 includes a plurality of locking apertures 250, a plurality of non-locking apertures 270, and one UR slot 310, wherein the respective axis of each aperture is generally directed inwardly towards the center of the underlying bone. Each of locking apertures 250 is assembled with one of first drill guides 330. Each of locking apertures 250, non-locking apertures 270, and UR slot 310 is sized for receiving first fastener 401. Each locking aperture 250 of shaft 110 is paired closely together with one of the non-locking apertures 270 to form four, spaced-apart, groupings or clusters, including a first grouping 120, a second grouping 130, a third grouping 140 and a fourth grouping 146, and corresponding to a first region 121, a second region 131, a third region 141, and a fourth region 147 on shaft 110. First grouping 120 opposes second grouping 130 about longitudinal axis 111 of plate 104, such that aperture axes 123 and 125 of first grouping 120 cross-over aperture axes 133 and 135 of second grouping 130. Similarly, third grouping 140 opposes fourth grouping 146.

During the surgical procedure, the surgeon may insert one of first fasteners 401 into each of regions 121, 131, 141, and 147. The surgeon may choose whether to select one of locking apertures 250 or one of non-locking apertures 270 for each region. In general, surgeons may choose to use locking apertures 250 if the underlying bone is not in condition to provide optimal engagement with the threads of shaft 110 of first fastener 401.

It should be appreciated that first DVR assembly 102 may be attached to the distal radius of a patient using only one type of bone fastener, i.e., a plurality of first fasteners 401 of varying lengths. In many current bone plate systems for fixation of the distal radius, a number of different types of fasteners are required. By using only one type, it is possible to reduce the number of instruments required in DVR kit 100, thereby reducing the size of container 10 (FIG. 4) and potentially lowering the overall cost of DVR kit 100. Using only one type of fastener also may help surgeons, especially those who are not greatly experienced doing the procedure, to perform the surgical procedure more quickly and without using the fasteners inappropriately.

FIG. 51 is an end view, FIG. 52 is a top view, and FIG. 53 is a perspective view of a second DVR assembly 152, which includes a second DVR plate 154 assembled with a plurality of first drill guides 330, and a plurality of second drill guides 340. Second DVR plate has a head 156, a neck 158 and a shaft 160 that extends along a longitudinal axis 161.

Head 156 includes a plurality of locking apertures 250, each of which is assembled with one of first drill guides 330 and is sized for receiving one of first fasteners 401. Each of locking apertures 250 of head 156 defines a desired, fixed trajectory, such that insertion of first fastener 401 into each locking aperture 250 of head 156 provides subchondral support of the articulation surface of the wrist joint of the distal radius.

Shaft 154 includes two of locking apertures 250, each of which is assembled with one of second drill guides 340 and is sized to receive one of second fasteners 451. Each of locking apertures 250 in shaft 154 is paired closely together with one of UR apertures 290, each of which is sized to receive one of second fasteners 451, to form a first grouping 170 that is spaced apart from a second grouping 180 along axis 161. First grouping 170 corresponds to a first region 171 and second grouping 180 corresponds to a second region 181 of plate 154. As for first DVR assembly 102, the axes 173, 175, 183 and 185 of the apertures of shaft 160 of second DVR assembly 152 are generally directed towards the center of the bone. Shaft 154 also includes BR slot 320 positioned approximately midway along axis 161.

Second DVR assembly 152 requires two types of fasteners, i.e., first fasteners 401 and second fasteners 451 of varying lengths. However, we envision that using two of second fasteners 451 in shaft 160 precludes the need to use four of first fasteners 401 in shaft 110 of first DVR assembly 102. This facilitates a quicker surgical procedure and eliminates the cost of the additional two fasteners.

Another feature of second DVR assembly 152 is the enhanced ability to draw the fractured bone fragments together axially as the fasteners are inserted. That is because, the dynamic compression that is achievable using UR apertures 290, if done in proper sequence, may be additive to the dynamic compression that is achievable using UR slot 310.

Figure 55:
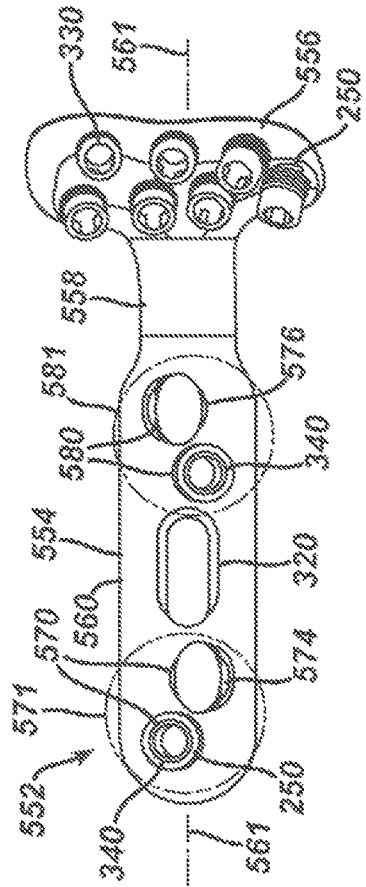
FIG. 55 is a top view of the third DVR assembly of FIG. 54.
Figure 56:
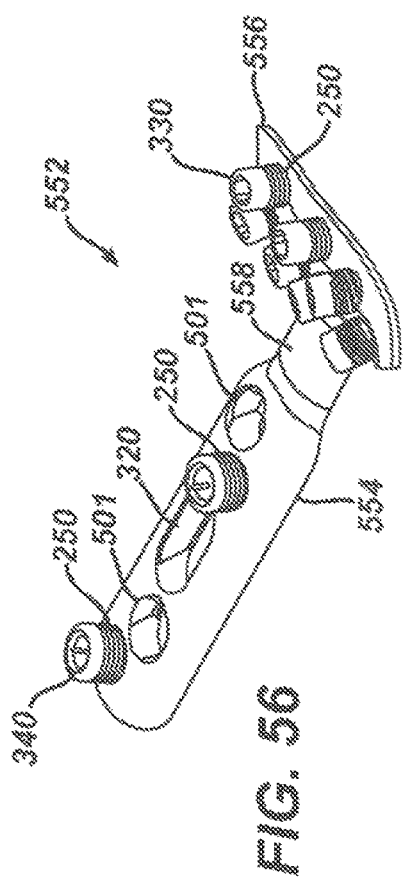
FIG. 56 is a perspective view of the third DVR assembly of FIG. 54.
Figure 54:
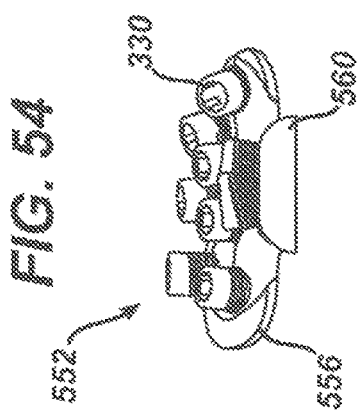
FIG. 54 is an end view of a third DVR assembly.

FIG. 54 is an end view, FIG. 55 is a top view, and FIG. 56 is a perspective view of a third DVR assembly 552, which includes a third DVR plate 554 assembled with a plurality of first drill guides 330, and a plurality of second drill guides 340. Third DVR plate 554 has a head 556, a neck 558 and a shaft 560 that extends along a longitudinal axis 561.

Head 556 includes a plurality of locking apertures 250, each of which is assembled with one of first drill guides 330 and is sized for receiving one of first fasteners 401. Each of locking apertures 250 of head 556 defines a desired, fixed trajectory, such that insertion of first fastener 401 into each locking aperture 250 of head 556 provides subchondral support of the articulation surface of the wrist joint of the distal radius.

Shaft 554 includes two of locking apertures 250, each of which is assembled with one of second drill guides 340 and is sized to receive one of second fasteners 451. Each of locking apertures 250 in shaft 554 is paired closely together with one of BR apertures 320, each of which is sized to receive one of second fasteners 451, to form a first grouping 570 that is spaced apart from a second grouping 580 along axis 561. First grouping 570 corresponds to a first region 571 and second grouping 180 corresponds to a second region 581 of plate 554. As for the previously described DVR assemblies 102 and 152, the axes of the apertures of shaft 560 of third DVR assembly 552 are generally directed towards the center of the bone. Shaft 554 also includes BR slot 320 positioned approximately midway along axis 561.

Third DVR assembly 552 requires two types of fasteners, i.e., first fasteners 401 and second fasteners 451 of varying lengths. However, as for second DVR assembly 152, we envision that using two of second fasteners 551 in shaft 560 precludes the need to use four of first fasteners 401 in shaft 110 of first DVR assembly 102. This facilitates a quicker surgical procedure and eliminates the cost of the additional two fasteners.

Again as with second DVR assembly 152, third DVR assembly 552 has the enhanced ability to draw the fractured bone fragments together axially as the fasteners are inserted since the dynamic compression that is achievable using BR apertures 501, if done in proper sequence, may be additive to the dynamic compression that is achievable using BR slot 320. However, third DVR assembly 552 has the additional ability to provide dynamic compression in either direction along axis 561 of plate 554.

Figure 57:
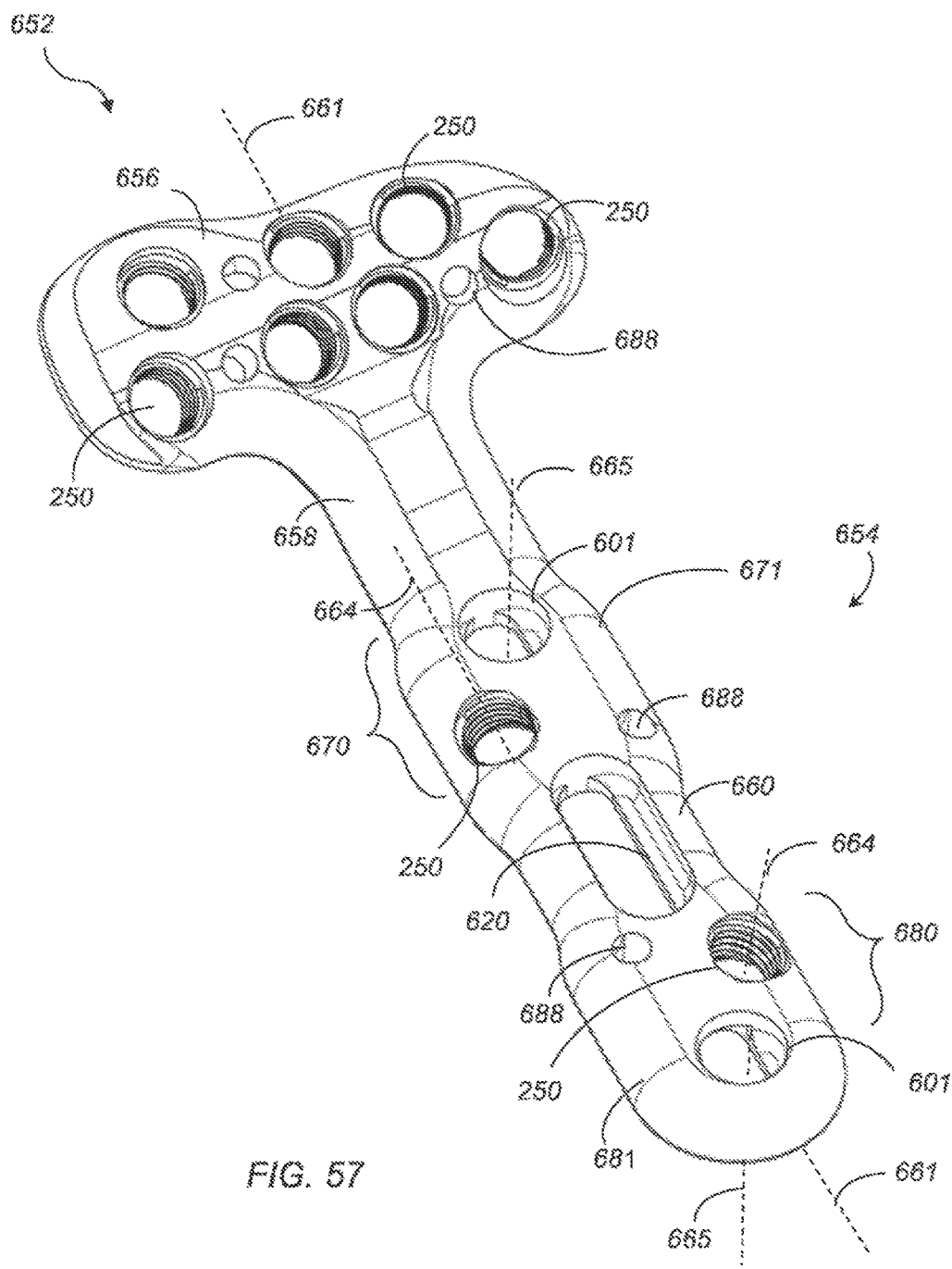
FIG. 57 is perspective view of the fourth DVR assembly.

FIG. 57 is a perspective view of a fourth DVR assembly 652, including a fourth DVR plate 654 that may be assembled with a plurality of first drill guides 330, and a plurality of second drill guides 340 (not shown but as discussed above with regard to the other DVR assemblies 102, 152, 552 shown in FIGS. 49-56). Fourth DVR plate 654 has a head 656, a neck 658, and a shaft 660 that extends along a longitudinal axis 661 of the DVR assembly 652. The head 656 may be wider than the shaft 660.

The head 656 may similarly include a plurality of spaced apart locking apertures 250, each of which may be preassembled with one of the first drill guides 330 (not shown) and sized for receiving one of the first fasteners 401. Each of the locking apertures 250 of the head 656 may define a desired, fixed trajectory, such that insertion of first fastener 401 into each locking aperture 250 of head 656 provides subchondral support of the articulation surface of the wrist joint of the distal radius.

As shown, the shaft 660 may also include a plurality of spaced-apart locking apertures 250, each of which may be assembled or preassembled with one of the second drill guides 340 (not shown) and is sized to receive one of the second fasteners 451. Each of the locking apertures 250 in the shaft 660 may be paired closely together with a non-locking aperture 601, each of which may be sized to receive one of the second fasteners 451. As shown, the shaft 660 may include a first grouping, or first aperture cluster 670, spaced apart from a second aperture cluster 680 generally along the longitudinal axis 661. The first aperture cluster 670 corresponds to a proximal region 671 of the shaft 660, and the second aperture cluster 680 corresponds to a distal region 681 of the shaft 660. In various aspects, the locking apertures 250 of the aperture clusters 670, 680 may generally be disposed on laterally opposed sides of the longitudinal axis 661.

The non-locking apertures 601 may be aligned on the longitudinal axis 661, and the locking apertures 250 may be offset from the longitudinal axis 661. Similar to the previously described DVR assemblies 102, 152, and 552, each locking aperture 250 of the shaft 660 may define an opening having an axis 664 that is generally inwardly directed towards a center of the fractured bone, which is oblique to the longitudinal axis 661. For example, in certain embodiments, the size of the implant head 656 may influence aspects of the design, including the angles of the longitudinal axis 664 of the locking aperture 250 with respect to the axis 665 normal or perpendicular to the plate shaft 660. By way of example, the angle between longitudinal axis 664 and normal axis 665 may be from about 10 degrees to about 30 degrees, depending in part on the size of the bone, such that a screw trajectory travels through a center region of the bone. In various embodiments, at least two respective threaded apertures 250 of the first and second aperture clusters 670, 680 define openings having axes that may be divergent from each other. The non-locking apertures 601 generally define an opening having an axis 665 normal to the longitudinal axis 661. As shown, the shaft 660 may also include a UR or BR aperture or slot 620 positioned approximately midway or centered along the longitudinal axis 661 and between the aperture clusters 670, 680. The bone plates 654 may also have one or more shaped openings 688 extending between the top and bottom surfaces of the bone plate 654, which may be configured to guide a K-wire passed therethrough.

Two types of fasteners, i.e., first fasteners 401 and second fasteners 451 of varying lengths may be used with the fourth DVR assembly 652. Again as with second and third DVR assemblies 152, 552, the fourth DVR assembly 652 also has the enhanced ability to draw the fractured bone fragments together axially as the fasteners are inserted since the dynamic compression that is achievable using UR or BR apertures 601, if done in proper sequence, may be additive to the dynamic compression that is achievable using BR slot 620. Thus, the fourth DVR assembly 652 has the additional ability to provide dynamic compression in either direction along the longitudinal axis 661 of the plate 654.

Figure 58:
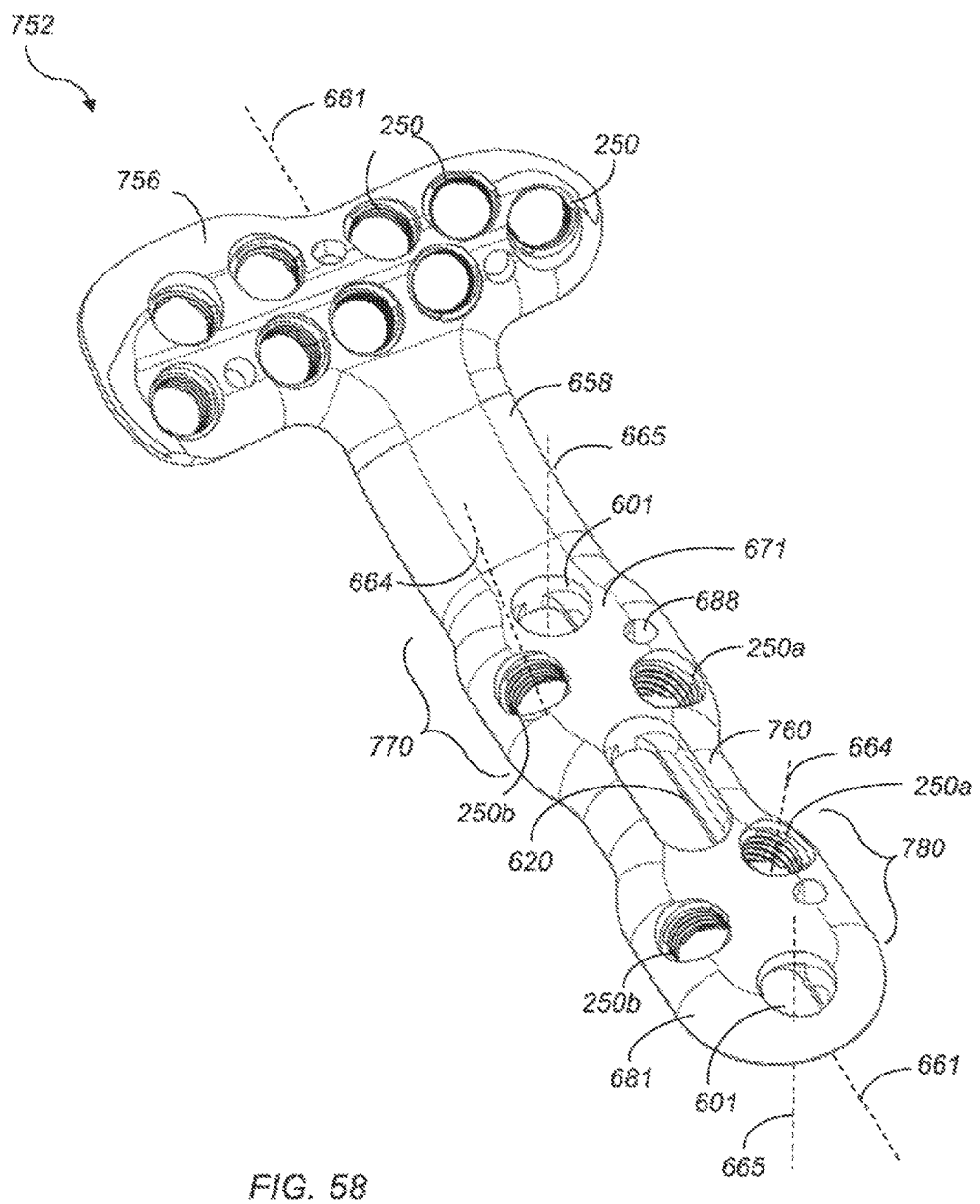
FIG. 58 is a perspective view of the fifth DVR assembly.

FIG. 58 is a perspective view of a fifth DVR assembly 752. The fifth DVR assembly 752 is similar in shape, design, and function to the fourth DVR assembly 652, and corresponding references numbers from FIG. 57 are used to indicate corresponding features in FIG. 58. Generally, the configuration of the bone plate 754 of FIG. 58 includes additional locking apertures 250 on both the head 756 and shaft 760 portions. For example, the aperture clusters 770 and 780 include two threaded, locking bone fastener apertures 250. As shown, two of the apertures 250a are on a first side of the longitudinal axis 661 and adjacent the BR slot 620, laterally opposed to two apertures 250b on a second side of the longitudinal axis 661, adjacent the non-locking apertures 601. Considering this design, in various aspects a physician may be able to install and conform the assembly 752 to the natural variations in an anatomy by installing non-locking screws first. During the installation of the non-locking screws, a physician may become more aware of the bone quality and further decide whether locking screws may be needed. For example, if a non-locking screw spins or otherwise loses its grip or is stripped, a locking screw may be inserted into aperture 250a and/or 250b as necessary.

The methods for implanting the bone plate system of FIGS. 57 and 58 are similar to the methods for implanting the DVR assemblies of the first through third assemblies 102, 152, 552. A bone plate is provided and aligned with the fractured bone. The methods may include shaping the bone plate, including inserting a first bone fastener into the bone through at least one of the unidirectionally ramped aperture and non-threaded bone fastener apertures in a direction normal to the longitudinal axis and dynamically compressing the bone along the longitudinal axis of the shaft portion of the bone plate. Once compressed and/or shaped, the method may include securing the bone plate, including inserting a second bone fastener into the bone through at least one of the threaded, locking bone fastener apertures in a direction oblique to the longitudinal axis and locking the bone plate to the bone.

We have shown and described various embodiments and examples. However, a person having ordinary skill in the art may modify the methods and devices described herein without departing from the overall concept. For instance, the specific materials, dimensions and the scale of drawings should be understood to be non-limiting examples. Accordingly, we do not intend the scope of the following claims to be understood as limited to the details of structure, materials or acts shown and described in the specification and drawings.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A bone plate system internally fixating a fractured bone of a patient, the system comprising:
   a bone plate including a head portion and a shaft portion having a longitudinal axis, the head portion being wider than the shaft portion, the bone plate further including:

a plurality of threaded, locking bone fastener apertures defined in the shaft portion and defining a respective plurality of threaded aperture axes; and a plurality of non-threaded, non-locking bone fastener apertures defined in the shaft portion, aligned on the longitudinal axis, and defining a respective plurality of non-threaded aperture axes, each non-threaded aperture axis being angled between about ten degrees and about thirty degrees with respect to each threaded aperture axis, each of the plurality of non-threaded bone fastener apertures being paired together with at least one of the plurality of the threaded bone fastener apertures to form a plurality of discrete aperture clusters, a first aperture cluster of the plurality of discrete aperture clusters being positioned about a proximal end of the shaft portion, a second aperture cluster of the plurality of discrete aperture clusters being positioned about a distal end of the shaft portion, the first and second aperture clusters including respective threaded, locking bone fastener apertures that are positioned on laterally opposed sides of the longitudinal axis; and a plurality of bone fasteners, each of the plurality of bone fasteners comprising a shaft and a head, each head being dimensioned and configured to threadedly engage each of the plurality of threaded, locking bone fastener apertures to provide a fixed angle locking construct, each head also being dimensioned and configured to directly engage each of the plurality of non-threaded, non-locking bone fastener apertures to provide a polyaxial compressive construct.

2. The bone plate system of claim 1, wherein each of the plurality of threaded, locking bone fastener apertures and each of the plurality of non-threaded, non-locking bone fastener apertures have the same nominal size.

3. The bone plate system of claim 1, wherein a surgeon may attach the bone plate to approximately the same part of the bone by selecting one of the threaded and non-threaded bone fastener apertures in any one of the first or second aperture clusters and inserting one of the plurality of bone fasteners therein.

4. The bone plate system of claim 1, wherein each threaded aperture axis is oblique to the longitudinal axis.

5. The bone plate system of claim 1, wherein each non-threaded aperture axis is normal to the longitudinal axis.

6. The bone plate system of claim 1, wherein each of the plurality of bone fasteners is configured to interchangeably act as one of a locking bone fastener and a non-locking bone fastener.

7. The bone plate system of claim 1, wherein:

each threaded aperture axis is inwardly directed toward a center of the bone; and the threaded aperture axes corresponding to the first and second aperture clusters are divergent from each other.

8. A bone plate system for internally fixating a fractured bone of a patient, the system comprising:

a bone plate defining a longitudinal axis, the bone plate including a head portion, the bone plate further including a shaft portion narrower than the head portion, the shaft portion further defining first and second threaded apertures positioned about proximal and distal ends of the shaft portion, respectively, and positioned on laterally opposed sides of the longitudinal axis, the first and second threaded apertures defining respective openings having respective first and second threaded aperture axes, the shaft portion defining first and second non-threaded apertures aligned on the longitudinal axis and positioned about the proximal and distal ends of the shaft portion, respectively, the first and second non-threaded apertures defining respective openings having respective first and second non-threaded aperture axes, each of the first and second non-threaded aperture axes being angled between about ten degrees and about thirty degrees with respect to each of the first and second threaded aperture axes; and a plurality of bone fasteners, each bone fastener, of the plurality of bone fasteners, comprising a shaft and a head, each head further being dimensioned and configured to threadedly engage each of the first and second threaded apertures to provide a locking, fixed angle construct, each head being dimensioned and configured to directly engage each of the first and second non-threaded apertures to provide a non-locking, polyaxial compressive construct.

9. The bone plate system of claim 8, wherein the first and second threaded apertures and the first and second non-threaded apertures define respective openings having the same nominal size.

10. The bone plate system of claim 8, wherein the first and second threaded aperture axes are oblique to the longitudinal axis.

11. The bone plate system of claim 8, wherein the first and second threaded aperture axes are divergent from each other.

12. The bone plate system of claim 8, wherein the first and second threaded aperture axes are inwardly directed toward a center of the bone.

13. The bone plate system of claim 8, wherein the first and second non-threaded aperture axes are normal to the longitudinal axis.

14. The bone plate system of claim 8, wherein each bone fastener, of the plurality of bone fasteners, is configured to interchangeably act as one of a locking bone fastener and a non-locking bone fastener.

15. A bone plate system for internally fixating a fractured bone of a patient, the system comprising:

a bone plate defining a longitudinal axis, the bone plate including a head portion, the bone plate further including a shaft portion narrower than the head portion, the shaft portion further defining first and second threaded apertures positioned about proximal and distal ends of the shaft portion, respectively, and positioned on laterally opposed sides of the longitudinal axis, the first and second threaded apertures defining respective threaded openings having respective first and second threaded aperture axes that are oblique to the longitudinal axis, divergent from each other, and inwardly directed toward a center of the bone, the shaft portion defining first and second non-threaded apertures aligned on the longitudinal axis and positioned about the proximal and distal ends of the shaft portion, respectively, the first and second non-threaded apertures defining respective non-threaded openings having respective first and second non-threaded aperture axes that are normal to the longitudinal axis, each of the first and second non-threaded aperture axes being angled between about ten degrees and about thirty degrees with respect to each of the first and second threaded aperture axes; and a plurality of bone fasteners, each bone fastener, of the plurality of bone fasteners, comprising a shaft and a head, each head further being dimensioned and configured to threadedly engage each of the first and second threaded apertures to provide a locking, fixed angle construct, each head being dimensioned and configured to directly engage each of the first and second non-threaded apertures to provide a non-locking, polyaxial compressive construct.

16. The bone plate system of claim 15, wherein the threaded openings and the non-threaded openings all have the same nominal size.

17. The bone plate system of claim 15, wherein each bone fastener, of the plurality of bone fasteners, is configured to interchangeably act as one of a locking bone fastener and a non-locking bone fastener.

* * * * *